United States Patent
Kadrmas et al.

(10) Patent No.: US 10,175,216 B2
(45) Date of Patent: Jan. 8, 2019

(54) REDUCED PARAMETER SPACE KINETIC MODELING SYSTEMS AND METHODS

(75) Inventors: Dan J. Kadrmas, North Salt Lake, UT (US); Mehmet Bugrahan Oktay, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 427 days.

(21) Appl. No.: 14/405,003

(22) PCT Filed: Jun. 5, 2012

(86) PCT No.: PCT/US2012/040885
§ 371 (c)(1),
(2), (4) Date: Apr. 16, 2015

(87) PCT Pub. No.: WO2013/184101
PCT Pub. Date: Dec. 12, 2013

(65) Prior Publication Data
US 2016/0216246 A1    Jul. 28, 2016

(51) Int. Cl.
*G01N 33/48* (2006.01)
*G01N 33/15* (2006.01)
*G06F 19/00* (2018.01)
*G06G 7/58* (2006.01)
*A61B 6/03* (2006.01)
*A61B 6/00* (2006.01)

(52) U.S. Cl.
CPC ........... *G01N 33/15* (2013.01); *G06F 19/704* (2013.01); *A61B 6/037* (2013.01); *A61B 6/4057* (2013.01)

(58) Field of Classification Search
None
See application file for complete search history.

(56) References Cited

U.S. PATENT DOCUMENTS

| 7,848,557 B2 | 12/2010 | Kadrmas et al. |
| 2007/0219729 A1 | 9/2007 | Peligrad et al. |
| 2008/0033291 A1 | 2/2008 | Rousso et al. |
| 2011/0060205 A1 | 3/2011 | Peligrad et al. |

OTHER PUBLICATIONS

Hong, Y.T. et al., "Kinetic Modeling Using Basis Functions Derived from Two-Tissue Compartmental Models with a Plasma Input Function: General Principle and Application to [$^{18}$F] Fluorodeoxyglucose Positron Emission Tomography," NeuroImage, vol. 51, pp. 164-172, 2010, Elsevier.
International Search Report and Written Opinion issued for PCT Application No. US2012/040885, dated Jan. 25, 2014, 10 pages.

*Primary Examiner* — Eric S Dejong
(74) *Attorney, Agent, or Firm* — Norton Rose Fulbright US LLP

(57) ABSTRACT

Systems, methods and devices are provided for fitting kinetic models to measurements of dynamic curves where the kinetic models give rise to nonlinear fitting equations in two or more unknowns that can be formulated so that they are linear in one or more of the unknown parameters and nonlinear in one or more of the unknown parameters. Such systems, methods and devices may be utilized to monitor and characterize the attributes of a given tracer such as a radioactive substance within a body, a drug within the body, a concentration of a substance within a particular medium, and the like.

31 Claims, 12 Drawing Sheets

REDUCED PARAMETER SPACE KINETIC MODELING SYSTEMS AND METHODS

BACKGROUND

The present invention relates to the art of fitting kinetic models. In particular, it relates to fitting mathematical models that describe how the behavior of a drug or substance (herein referred to as a "tracer") changes as a function of time in a physiologic system to measurements of such dynamic processes. The task of fitting kinetic models arises in a wide variety of fields, including but not limited to drug development, preclinical and diagnostic imaging, and radiation dosimetry.

The prototypical kinetic model is a compartment model, which describes how the tracer (drug or substance) exchanges between the input source (typically arterial blood) and different tissue locations and/or different chemical forms occupying the same physical space ("compartments"). However, a number of other types of kinetic models exist, such as those that model the system as a sum of exponentials or other functions, often convolved with the input source function. In a typical application, a series of measurement of the tracer concentration are made sequentially over period of minutes, hours, or days, as the tracer distributes physiologically. Measurements of the tracer concentration in the source input (e.g. arterial blood) may also be made in some cases. These data in aggregate measure how the tracer concentration changes as a function of time—i.e., a dynamic curve. A mathematical model that predicts the dynamic curve in terms of meaningful and quantifiable parameters is then fit to the measured data, providing estimates of the model parameters that relate to the underlying physiologic processes controlling the tracer distribution. These model parameters are the desired endpoints of the kinetic model fitting process.

The nature of how tracers distribute in physiologic systems gives rise to complex modeling equations that include "nonlinear" terms. Such nonlinear equations are much more difficult to solve than linear equations, which can often be solved analytically in a single step. Mathematical fits to nonlinear equations cannot be solved in a single step, but instead require that a number of possible solutions be tested in order to find the solution that most-closely matches the measured data.

The current state of the art in kinetic modeling is to use iterative nonlinear fitting algorithms to minimize a least squares-type objective function, providing an estimate of the least-squares (or weighted least-squares) solution. These nonlinear least-squares (NLLS) algorithms are often considered to provide the most robust kinetic model fits, but have a number of shortcomings. The multi-dimensional nonlinear fitting space is complex and variable, including local minima, ridges, and valleys that can confound the iterative fitting algorithm. As a result, the NLLS solution is dependent on the initial conditions provided by the user, requiring in many cases that the user manually provide a set of initial conditions that is already an approximate match for the measured dynamic curve being fit. The number of iterations and iterative stopping criterion need to be carefully managed. Once the fit is obtained, careful attention to quality assurance must be performed in order to ensure that the resultant fit closely-matches the measured data; even then, however, one can never be certain that the true least-squares best fit has been obtained.

More robust versions of NLLS fitting algorithms have been tested, which resort to restarting the fits over and over again with changing conditions in order to escape local minima and reduce the dependency on initial conditions. Such approaches, however, tend to be very computationally demanding. Alternative algorithms, such as simulated annealing, use related schemes to increase the chances of obtaining the true global minimum fit. However, these are also very computational demanding, requiring extensive computer power and time for each fit. A variety of other approaches have been and are under development, including a variety of linearized fitting approaches, graphical analysis methods, and basis function approaches. While these methods show promise for some applications, each makes certain approximations or has other complicating factors that fall short of the ideal fitting solution.

These earlier works have not resulted in a kinetic model fitting approach that is simple, fast, effective, and robustly finds the true best-fit solution in all cases in the presence of real-world complicating factors such as high levels of noise in the measurements.

BRIEF SUMMARY

The present application provides for systems, methods and devices configured for fitting kinetic models to measurements of dynamic curves where the kinetic models give rise to nonlinear fitting equations in two or more unknown parameters that can be re-formulated so that they are linear in one or more of the unknown parameters and nonlinear in one or more of the unknown parameters. Embodiments provide very fast, simple, effective, and robust fits to such kinetic models.

In one aspect, a method for fitting kinetic models for dynamic imaging (dynamic positron emission tomography (PET), dynamic contrast enhanced magnetic resonance imaging [DCE-MRI], dynamic single-photon emission computed tomography (SPECT), dynamic contrast-enhanced x-ray CT), including individual time-activity curves (e.g. from a region-of-interest), is provided. Further, embodiments may fit kinetic models for full parametric imaging (where the time-activity curve for each individual voxel is fit, producing images of each model parameter="parametric images").

In another aspect, a method for fitting pharmacokinetic models that describe changes in drug concentrations as functions of time using either noncompartmental or compartmental analysis is provided. In such embodiments, modeling equations may include at least two unknown parameters where the equation(s) can be reformulated to be linear in at least one unknown parameter and nonlinear in at least one unknown parameter.

It is noted that the methods described herein may be implemented in any circumstance that kinetic models may be utilized, e.g. in radiation dosimetry calculations, peritoneal dialysis kinetic modeling, modeling general biological systems, and the like. Further, these methods may be configured to model single or multiple tracers in accordance with the specific application.

The foregoing has outlined rather broadly the features and advantages of the present application in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of embodiments described herein, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present embodiments.

BRIEF DESCRIPTION OF THE DRAWINGS

For a more complete understanding, reference is now made to the following descriptions of example embodiments taken in conjunction with the accompanying drawings, in which.

DETAILED DESCRIPTION

Figure 1A:
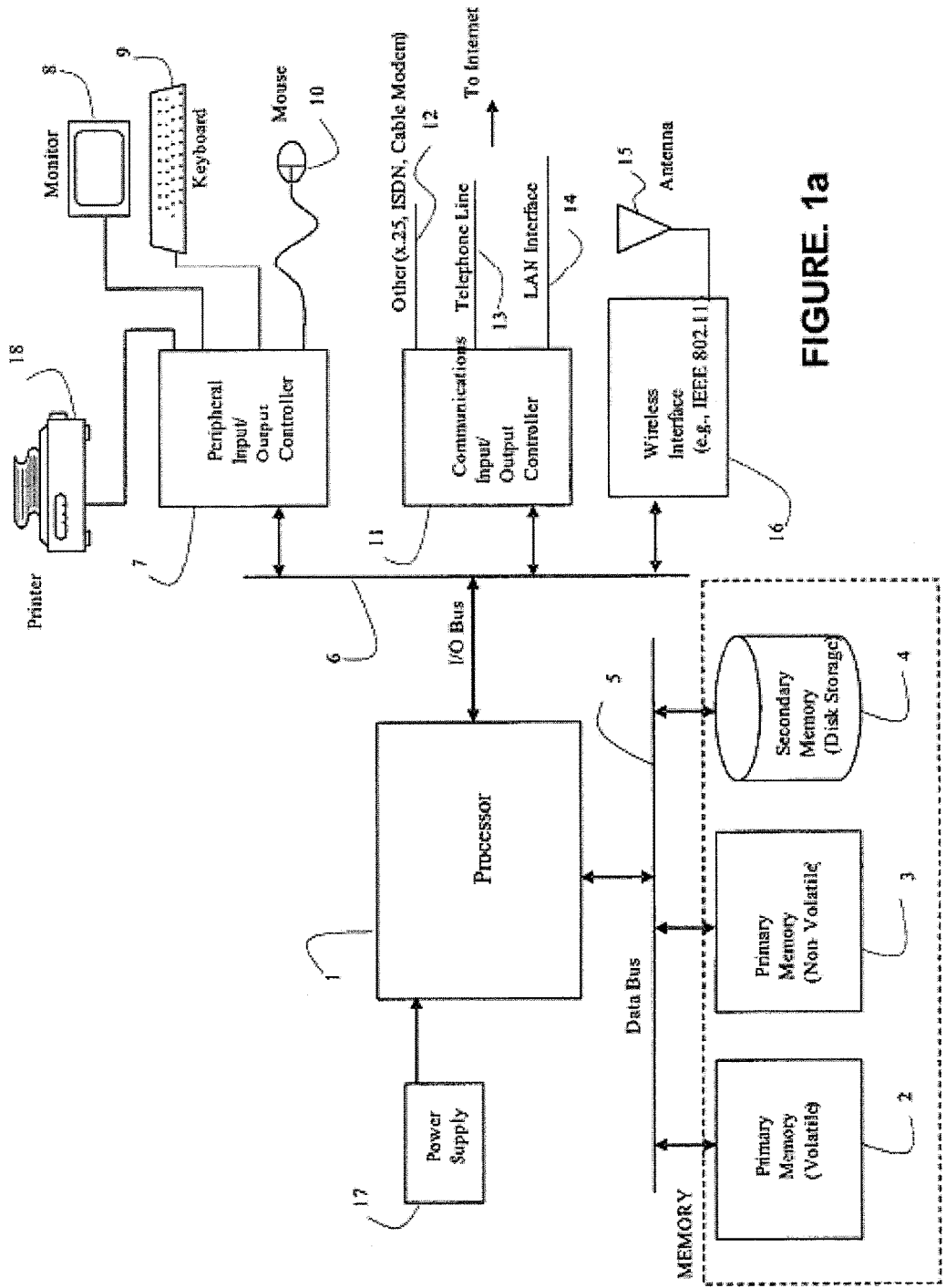
FIG. 1a illustrates one embodiment of a computing device that can be used to practice aspects of embodiments.

Before the present methods and systems are disclosed and described, it is to be understood that this invention is not limited to specific synthetic methods, specific components, or to particular compositions, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The different aspects and applications of the kinetic modeling systems and methods give rise to different, but analogous, terminology. Much of the description of the invention is described in the context of its embodiment for dynamic positron emission tomography (PET) and dynamic single-photon emission computed tomography (SPECT) imaging. However, the proposed kinetic modeling systems and methods are broadly applicable to many fields, and the description in terms of this embodiment are not intended to be limiting but rather are intended to apply across the other embodiments.

Herein, the term "tracer" is used to generically identify the imaging agent, radiotracer, pharmaceutical, drug, compound, radionuclide, or other substance whose concentration or distribution is being modeled over time. Similarly, the term "time-activity curve" is used to generically identify the timecourse of the tracer which, in the various embodiments, may more specifically describe (but is not limited to) an amount, concentration, radioactivity level, or other quantitative measure that changes over time.

The term "kinetic" is used to identify processes under discussion that involve changes in time. In the various embodiments, the terms "biokinetic," "dynamic," or "temporal" may also be used synonymously.

The act of "fitting" is identified as the act of estimating the model parameters that match the modeled time-activity curve in its various embodiments (tracer concentration curve, drug concentration curve, etc.) to the measurements. The "match" between the modeled curve and the measured data is mathematically quantified in terms of a fitting criterion, herein referred to as the "objective function." The objective function may be mathematically defined in various ways, including but not limited to the chi-squared function, the weighted sum-squared error (WSSE), the least-squares residual, or the weighted-least squares residual. The best fit is defined by the set of model parameters that either minimize or maximize the objective function, depending on which objective function is selected for the particular application. Without loss of generality, the best-fit is referred to as minimizing the objective function, as it is more common for the best-fit criterion to be minimized rather than maximized.

As will be appreciated by one skilled in the art, embodiments may be implemented as a method, a data processing system, or a computer program product. Implementations of embodiments may take the form of a computer program product on a computer-readable storage medium having computer-readable program instructions (e.g., computer software) embodied in the storage medium. More particularly, implementations of embodiments may take the form of web-implemented computer software. Any suitable computer-readable storage medium may be utilized including hard disks, CD-ROMs, optical storage devices, or magnetic storage devices.

Embodiments are also described below with reference to block diagrams and flowchart illustrations of methods, apparatuses, systems and computer program products according to an embodiment of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

In the embodiments referenced herein, a "computer" or "computing device" may be referenced. Such computer may be, for example, a mainframe, desktop, notebook or laptop, a hand held device such as a data acquisition and storage device, or it may be a processing device embodied within (or used in conjunction with) another apparatus such as, for example, a scanner used for tomography (e.g. PET, SPECT, MRI, and CT scanning devices), an image processing or data processing computer workstation, chemical analysis processors, and the like. In some instances the computer may be a "dumb" terminal used to access data or processors over a network. Turning to FIG. 1a, one embodiment of a computing device is illustrated that can be used to practice aspects of embodiments. In FIG. 1a, a processor 1, such as a microprocessor, is used to execute software instructions for carrying out the defined steps. The processor 1 receives power from a power supply 17 that also provides power to the other components as necessary. The processor 1 communicates using a data bus 5 that is typically 16 or 32 bits wide (e.g., in parallel). The data bus 5 is used to convey data and program instructions, typically, between the processor and memory. In the present embodiment, memory can be considered primary memory 2 that is RAM or other forms which retain the contents only during operation, or it may be non-volatile 3, such as ROM, EPROM, EEPROM, FLASH, or other types of memory that retain the memory contents at all times. The memory could also be secondary memory 4, such as disk storage, that stores large amount of data. In some embodiments, the disk storage may communicate with the processor using an I/O bus 6 instead or a dedicated bus (not shown). The secondary memory may be a floppy disk, hard disk, compact disk, DVD, or any other type of mass storage type known to those skilled in the computer arts.

The processor 1 also communicates with various peripherals or external devices using an I/O bus 6. In the present embodiment, a peripheral I/O controller 7 is used to provide standard interfaces, such as RS-232, RS422, DIN, USB, or other interfaces as appropriate to interface various input/output devices. Typical input/output devices include local printers 18, a monitor 8, a keyboard 9, and a mouse 10 or other typical pointing devices (e.g., rollerball, trackpad, joystick, etc.).

The processor 1 typically also communicates using a communications I/O controller 11 with external communication networks, and may use a variety of interfaces such as data communication oriented protocols 12 such as X.25, ISDN, DSL, cable modems, etc. Such interfaces may be used to receive input data from an external device, such as an imaging system or another diagnostic system. Alternatively, these interfaces may be used to export data for remote processing or to provide results from processing which takes place locally. The communications controller 11 may also incorporate a modem (not shown) for interfacing and communicating with a standard telephone line 13. Finally, the communications I/O controller may incorporate an Ethernet interface 14 for communicating over a LAN. Any of these interfaces may be used to access a wide area network such as the Internet, intranets, LANs, or other data communication facilities.

Finally, the processor 1 may communicate with a wireless interface 16 that is operatively connected to an antenna 15 for communicating wirelessly with another device, using for example, one of the IEEE 802.11 protocols, 802.15.4 protocol, or a standard 3G/4G wireless telecommunications protocols, such as CDMA2000 1×EV-DO, GPRS, W-CDMA, or other protocol.

Figure 1B:
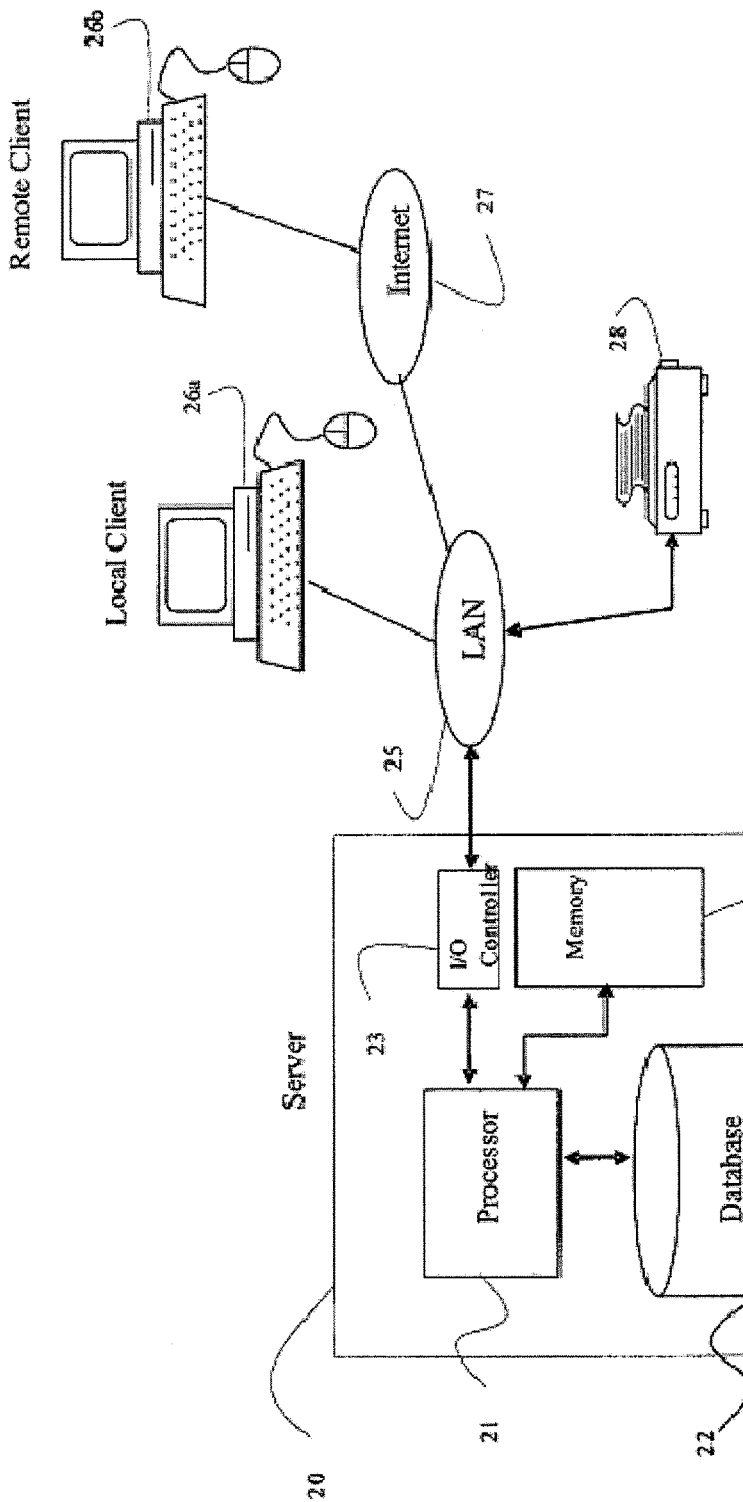
FIG. 1b illustrates an alternative embodiment of a processing system.

An alternative embodiment of a processing system that may be used is shown in FIG. 1b. In this embodiment, a distributed communication and processing architecture is shown involving a server 20 communicating with either a local client computer 26a or a remote client computer 26b. The server 20 typically comprises a processor 21 that communicates with a database 22, which can be viewed as a form of secondary memory, as well as primary memory 24. The processor also communicates with external devices using an I/O controller 23 that typically interfaces with a LAN 25. The LAN may provide local connectivity to a networked printer 28 and the local client computer 26a. These may be located in the same facility as the server, though not necessarily in the same room. Communication with remote devices typically is accomplished by routing data from the LAN 25 over a communications facility to a wide area network 27, such as the Internet. A remote client computer 26b may execute a web browser, so that the remote client 26b may interact with the server as required by transmitted data through the wide area network 27, over the LAN 25, and to the server 20. In some embodiments, a remote client may be implemented as part of a tomography scanning system, and information provided therefrom may be processed by one or more of the remote client or within server 20. Embodiments may return processed data to the location of the remote client, or such data may be maintained at the server location.

Those skilled in the art of data networking will realize that many other alternatives and architectures are possible and can be used to practice the preferred embodiments. The embodiments illustrated in FIGS. 1a and 1b can be modified in different ways and be within the scope of the present invention as claimed.

Described herein are embodiments of a method of fitting kinetic models to dynamic measurements of one or more tracers or other agents, where the kinetic model or models has two or more unknown parameters, where the modeling equations can be formulated to be linear in at least one unknown parameter and nonlinear in at least one unknown parameter, and where the fit is performed either to a single dynamic measurement or to a group of measurements simultaneously (e.g. dynamic parametric imaging).

A number of kinetic models are receptive to the use of the described Reduced Parameter Space Kinetic Modeling systems and methods, including a variety of compartment models as well as any number of noncompartmental models. Embodiments described utilize a modeling equation that contains at least two unknowns, where the equation can be formulated in such a way that it is linear in at least one reformulated unknown parameter and nonlinear in at least one reformulated unknown parameter. Further, the original model parameters can be recovered from the fitted reformulated unknown parameters. These steps are described in detail below using specific instances of common kinetic models, e.g. positron emission tomography (PET) and single-photon emission computed tomography (SPECT) (for descriptive purposes only). As such, quantities are described as tracer radioactivity concentrations. However, the systems and methods are not limited to only these models, but rather are applicable to all kinetic models which may incorporate with methods and techniques described herein, e.g. using other dynamic imaging modalities and non-imaging applications of kinetic modeling.

The described Reduced Parameter Space Kinetic Modeling systems and methods comprise the reformulation of the modeling equations into separated linear and nonlinear unknowns, followed by application of the constraint that the fitting solution space only include possible solutions that minimize the fitting objective function in the linear sense. Application of this constraint effectively solves the estimation of the reformulated linear parameters, such that the overall fitting problem is reduced to estimation of the reformulated nonlinear unknown parameters. Any number of nonlinear fitting algorithms can be used to estimate the best-fit reformulated nonlinear parameters, and the value of the Reduced Parameter Space technique lies in the greatly reduced complexity of the nonlinear fitting problem that arises from the reformulation and constraint listed above. Once the reduced nonlinear fitting problem is solved, the fitted reformulated parameters are converted mathematically back into the original model parameters, whose estimation is the primary objective of the fit.

Figure 2:
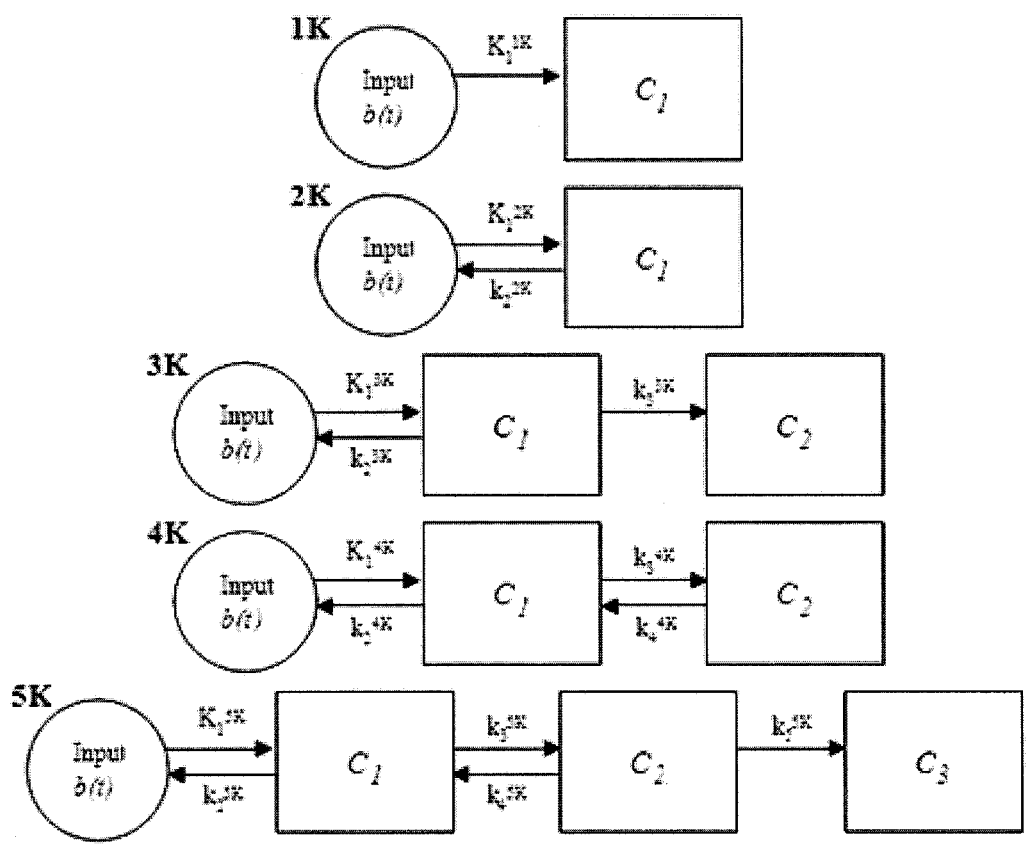
FIG. 2 illustrates several generic compartment models in order of increasing complexity, along with a shorthand nomenclature to quickly reference each generic model.

The described mathematical reformulations will be presented and discussed in the context of compartment modeling, though the technique is generally applicable to other kinetic models (as well as other mathematical problems) where the solution equations are nonlinear and contain a mixture of scalar coefficients and nonlinear temporal terms. FIG. 2 presents several generic compartment models in order of increasing complexity, along with a shorthand nomenclature to reference each generic model. Generic serial compartment models, each consisting of an input driving 1-3 tissue compartments in series that exchange according to the labeled rate parameters. A shorthand nomenclature to quickly reference each generic model as shown will be used. For example, the "3K" model refers to a model with input plus two additional compartments and three rate parameters.

Specific considerations of other compartment models, e.g. those with more compartments or whose compartments do not fall in series, are not included in this application; however, the proposed parameter space reduction techniques are generally applicable to such models as well.

Exchange between connected compartments is governed by linear differential equations of the form:

$$\frac{dC_i}{dt} = \sum k_{in} C_{in} - \left(\sum k_{out}\right) C_i, \quad (1)$$

where the subscripts in and out refer to rate parameters that describe exchange into (from compartment $C_{in}$) or out of compartment $C_i$, respectively. The input function, b(t), drives the system; it is generally assumed to be known either from direct measurement or some other estimation technique. The imaging measurement R(t) typically cannot measure each compartment individually; rather, the imaging signal comprises the sum over all compartments, $C(t;b(t),\{k_i\})$, often with the addition of a vascular term due to imaging signal from whole-blood, B(t):

$$R(t) = f_B B(t) + (1 - f_B) C(t; b(t), \{k_i\}), \quad (2)$$

where $f_B$ is the fractional contribution of B(t) to the imaging measurement. The rate parameters $\{k_i\}$, along with $f_B$, are the unknown parameters of the model to be estimated. While the differential equations are linear in the unknown parameters, the solution equations are nonlinear, containing weighted sums of exponentials (with unknowns in the exponent) convolved with the input function. As such, fitting compartment models to measured datasets involves a nonlinear minimization problem.

Generalized Kinetic Modeling Reformulation into Separable Linear and Nonlinear Unknown Parameters Consider a kinetic model of the general form:

$$R(t) = \sum_i \kappa_i S_i(t; v_i), \quad (3)$$

where R(t) is the modeled time-activity curve; $\kappa_i$ and $v_i$ are scalar parameters; and $S_i(t;v_i)$ are temporal terms that depend on time as well as (possibly) scalar parameter(s) $v_i$. Models of this form are linear in $\kappa_i$ but nonlinear in $v_i$, and can represent a variety of specific kinetic models. Without loss of generality, we will work with a specific form of (3) that is directly applicable to compartment modeling.

Let $\kappa_B$, $\kappa_b$, $\kappa_1$, $\kappa_2$, $v_1$, and $v_2$ be scalar parameters that will be further described below, and let B(t) be the whole-blood activity concentration.

TABLE 1

GLOSSARY OF EQUATION TERMS

| Term | Definition |
|---|---|
| b(t) | Input function |
| ḃ(t) | Integral of b(t) over time |
| B(t) | Tracer concentration in whole-blood |
| $f_B$ | Fractional contribution of B(t) to the imaging measurement |

TABLE 1-continued

GLOSSARY OF EQUATION TERMS

| Term | Definition |
|---|---|
| $\kappa_B, \kappa_b, \kappa_1, \kappa_2$ | Linear parameters of the Reduced Parameter Space formulations |
| $v_1, v_2$ | Nonlinear parameters of the Reduced Parameter Space formulations |
| $K_1, k_2$-$k_5$ | Rate constants for 1K-5K serial compartment models |
| $K_{net}$ | Net influx macroparameter, $K_{net} = K_1 k_3/(k_2 + k_3)$ |
| $R(t)$ | Modeled time-activity curve |
| $S_1, S_2$ | Temporal terms defined in equations (5) and (6) |
| $V_D$ | Volume of Distribution, $V_D = K_1/k_2$ |

Further, define the following temporal terms that depend on the input function, b(t), as well as certain scalar parameters:

$$\check{b}(t) \equiv \int_0 b(\tau) d\tau, \quad (4)$$

$$S_1(t;v_1;b) \equiv \int_0 e^{-v_1(t-\tau)} b(\tau) d\tau, \text{ and} \quad (5)$$

$$S_2(t;v_1,v_2;b) \equiv \int_0 (e^{-v_2(t-\tau)} - e^{-v_1(t-\tau)}) b(\tau) d\tau \quad (6)$$

We can then write the generalized equation:

$$R(t) = \kappa_B B(t) + \kappa_b \check{b}(t) + \kappa_1 S_1(t;v_1;b) + \kappa_2 S_2(t;v_1,v_2;b) \quad (7)$$

As shown below, using appropriate definitions of $\kappa_B$, $\kappa_b$, $\kappa_1$, $\kappa_2$, $v_1$, and $v_2$, this general formulation encompasses the solution equations for 1K-5K serial compartment models, as well as other kinetic models of similar form.

In all cases below we define $\kappa_B \equiv f_B$, and the first term represents the contribution from whole-blood. The remaining scalar parameters take on different values depending on the compartment model:

1K Model: 1 Tissue Compartment with K1

Let: $\kappa_b^{(1K)} = (1-f_B)K_1$, $\kappa_1^{(1K)} = 0$, and $\kappa_2^{(1K)} = 0$.

Then $R^{(1K)}(t) = \kappa_B B(t) + \kappa_b^{1K} \check{b}(t)$, giving $$R^{(1K)}(t) = f_B B(t) + (1-f_B) K_1 \int_0 b(\tau) d\tau, \quad (8)$$

which we recognize as the conventional 1K compartment model solution equation. We have chosen to include the $(1-f_B)$ weighting factor in the tissue term for generality here and throughout, though many particular applications of the 1K model do not include this factor. Similarly, specific applications may or may not include the vascular term, $f_B B(t)$, which again has been included here to preserve generality.

2K Model: 1 Tissue Compartment with K1, k2

Let: $v_1^{(2K)} = k_2$, $\kappa_b^{(2K)} = 0$, $\kappa_1^{(2K)} = (1-f_B)K_1$, and $\kappa_2^{(2K)} = 0$.

Then: $R^{(2K)}(t) = \kappa_B B(t) + \kappa_1^{(2K)} S_1(t;v_1^{(2K)};b)$, giving $$R^{(2K)}(t) = f_B B(t) + (1-f_B) K_1 \int_0 e^{-k_2(t-\tau)} b(\tau) d\tau. \quad (9)$$

Under the constraint that each parameter is non-negative, we recognize this as the standard formulation of the 2K compartment model solution equation.

3K Model: 2 Tissue Compartments with K1, k2-k3

Let: $v_1^{(3K)} = k_2 + k_3$, $\kappa_b^{(3K)} = (1-f_B)\frac{K_1 k_3}{k_2 + k_3}$, \quad (10)

$\kappa_1^{(3K)} = (1-f_B)\frac{K_1 k_2}{k_2 + k_3}$, and $\kappa_2^{(3K)} = 0$.

Then: $R^{(3K)}(t) = \kappa_B B(t) + \kappa_b^{(3K)} \check{b}(t) + \kappa_1^{(3K)} S_1(t;v_1^{(3K)};b)$, giving $$R^{(3K)}(t) = f_B B(t) +$$

$$(1-f_B)\left\{\frac{K_1 k_3}{k_2+k_3}\int_0^t b(\tau)d\tau + \frac{K_1 k_2}{k_2+k_3}\int_0^t e^{-(k_2+k_3)(t-\tau)} b(\tau)d\tau\right\}.$$

Under the constraint that each parameter is non-negative, we recognize this as the standard formulation of the 3K compartment model solution equation.

4K Model: 2 Tissue Compartments with K1, k2-k4

Let: $v_{1,2}^{(4K)} \equiv \frac{1}{2}\left\{(k_2+k_3+k_4) \pm \sqrt{(k_2+k_3+k_4)^2 - 4k_2 k_4}\right\}$, $\kappa_b^{(4K)} = 0$, $\kappa_1^{(4K)} = (1-f_B)K_1$, and $$\kappa_2^{(4K)} = \frac{(1-f_B)K_1}{(v_2^{(4K)} - v_1^{(4K)})}(v_2^{(4K)} - k_3 - k_4).$$

Then: $R^{(4K)}(t) =$ $\kappa_B B(t) + \kappa_b^{(4K)} \check{b}(t) + \kappa_1^{(4K)} S_1(t;v_1^{(4K)};b) + \kappa_2^{(4K)} S_2(t;v_1^{(4K)}, v_2^{(4K)};b)$, giving $R^{(4K)}(t) = f_B B(t) + (1-f_B)K_1 \int_0^t e^{-v_1^{(4K)}(t-\tau)} b(\tau) d\tau +$ $$\frac{(1-f_B)K_1}{(v_2^{(4K)} - v_1^{(4K)})}(v_2^{(4K)} - k_3 - k_4)\int_0^t \left(e^{-v_2^{(4K)}(t-\tau)} - e^{-v_1^{(4K)}(t-\tau)}\right) b(\tau) d\tau.$$

Changing notation:

$$l_2 = v_1, \, l_1 = v_2, \, \beta_1 = \frac{1}{(l_2 - l_1)}(k_3 + k_4 - l_1),$$

and $\beta_2 = \frac{1}{(l_2 - l_1)}(l_2 - k_3 - k_4),$ and using the relation $1 - \beta_1 = \beta_2$, we obtain:

$$R^{(4K)}(t) = f_B B(t) + (1-f_B)K_1\left\{\frac{(k_3+k_4-l_1)}{(l_2-l_1)}\int_0^t e^{-l_1(t-\tau)} b(\tau) d\tau + \right. \quad (11)$$

$$\left. \frac{(l_2 - k_3 - k_4)}{(l_2 - l_1)} \int_0^t e^{-l_2(t-\tau)} b(\tau) d\tau\right\}.$$

In addition to constraining each parameter to be non-negative, we further consider the constraint $v_2 < v_1$ (equivalent to requiring $k_2$ to be positive and $k_3$ and $k_4$ to be non-negative) and $\kappa_2 < \kappa_1$ (this constraint is discussed below) in order to limit the solution space to regions that represent valid compartment models. Under these constraints, we recognize this as the solution to the 4K compartment model equations.

5K Model: 3 Tissue Compartments with K1, k2-k5

Adding a third tissue compartment for the 5K model results in a more lengthy derivation. In consideration of space, we leave aside the details and provide the values of $\kappa_B$, $\kappa_b$, $\kappa_1$, $\kappa_2$, $\upsilon_1$, and $\upsilon_2$ that represent the 5K model solution using the generalized formulation of equation (7):

$$v_{1,2}^{(5K)} = \frac{1}{2}\left\{\frac{(k_2+k_3+k_4+k_5) \pm}{\sqrt{(k_2+k_3+k_4+k_5)^2 - 4(k_2k_4+k_2k_5+k_3k_5)}}\right\}, \quad (12)$$

$$\kappa_b^{(5K)} = (1-f_B)\frac{K_1 k_3 k_5}{k_2 k_4 + k_2 k_5 + k_3 k_5},$$

$$\kappa_1^{(5K)} = (1-f_B)K_1\left(\frac{k_2(k_4+k_5)}{k_2 k_4 + k_2 k_5 + k_3 k_5}\right), \text{ and}$$

$$\kappa_2^{(5K)} = \frac{(1-f_B)K_1}{(v_1^{(5K)} - v_2^{(5K)})}\left[(k_3+k_4+k_5-v_2^{(5K)}) - \frac{k_3 k_5}{v_2^{(5K)}}\right].$$

This reformulation represents a valid 5K model under the constraints that each parameter is non-negative, $\upsilon_2 < \upsilon_1$, and $\kappa_2 < \kappa_1$.

Other Models

The generalized formulation of equation (3) can also be used to represent a number of other compartment models and well as other kinetic model formulations, for which Reduced Parameter Space reformulations similar to those shown below could also be derived. The examples shown here cover the most-commonly used compartment models in dynamic PET and SPECT imaging for a number of different radiotracers.

Discretization of the Model

For dynamic imaging, the measured data are generally discrete samples in time. Depending on the modality and other factors, two discretization schemes are commonly encountered—instantaneous samples, and samples averaged over time-frame durations. For each case we define the following discretizations, where $j=1 \ldots M$ represents the time (time-frame) index (recall that $\breve{b}(t) = \int_0^t b(\tau)d\tau$):

Instantaneous Samples:

$$R_j = R(t_j) \quad B_j = B(t_j)$$

$$\breve{b}_j = \breve{b}(t_j)$$

$$S_{1,j}(\upsilon_1;b) \equiv S_1(t_j;\upsilon_1;b)$$

$$S_{2,j}(\upsilon_1,\upsilon_2;b) \equiv S_2(t_j;\upsilon_1,\upsilon_2;b) \quad (13)$$

Averaged Over Time-Frame Durations:

$$R_j \equiv \frac{1}{(t_{j2}-t_{j1})}\int_{t_{j1}}^{t_{j2}} R(\tau)d\tau \quad B_j \equiv \frac{1}{(t_{j2}-t_{j1})}\int_{t_{j1}}^{t_{j2}} B(\tau)d\tau \quad (14)$$

$$\breve{b}_j \equiv \frac{1}{(t_{j2}-t_{j1})}\int_{t_{j1}}^{t_{j2}} \breve{b}(\tau)d\tau$$

$$S_{1,j}(\upsilon_1;b) \equiv \frac{1}{(t_{j2}-t_{j1})}\int_{t_{j1}}^{t_{j2}} S_1(\tau;\upsilon_1;b)d\tau$$

$$S_{2,j}(\upsilon_1,\upsilon_2;b) \equiv \frac{1}{(t_{j2}-t_{j1})}\int_{t_{j1}}^{t_{j2}} S_2(\tau;\upsilon_1,\upsilon_2;b)d\tau$$

In addition, we distinguish between modeled values $\hat{R}_j$ and noisy measurements $\tilde{R}_j$ using a carat and tilde, respectively.

Using either discretization, the generalized kinetic model at each time sample j is written:

$$\hat{R}_j = \kappa_B B_j + \kappa_b \breve{b}_j + \kappa_1 S_{1,j}(\upsilon_1;b) + \kappa_2 S_{2,j}(\upsilon_1,\upsilon_2;b). \quad (15)$$

The model fitting problem amounts to finding the values of the parameters $\kappa_B$, $\kappa_b$, $\kappa_1$, $\kappa_2$, $\upsilon_1$ and $\upsilon_2$ that minimize some objective function. We consider the weighted least-squares (WLS) criterion, and write the weighted sum-squared error objective function as:

$$WSSE = \sum_{j=1}^{T} w_j(\hat{R}_j - \tilde{R}_j)^2 \quad (16)$$

$$= \sum_{j=1}^{T} w_j\left[\kappa_B B_j + \kappa_b \breve{b}_j + \kappa_1 S_{1,j}(\upsilon_1;b) + \kappa_2 S_{2,j}(\upsilon_1,\upsilon_2;b) - \tilde{R}_j\right]^2$$

where $w_j$ are the weights for each time sample j.

Reducing the Parameter Space to Include Solutions that Minimize the Objective Function in the Linear Sense We have shown that the generalized formulation of equation (7) can be used to represent a number of commonly used compartment models. Note that this formulation is explicitly linear in parameters $\kappa_B$, $\kappa_b$, $\kappa_1$, and $\kappa_2$, and nonlinear in $\upsilon_1$ and $\upsilon_2$ (which appear in the temporal components $S_1$ and $S_2$). Furthermore, the temporal components $S_1$ and $S_2$ are independent of the scalar coefficients ($\kappa_B$, $\kappa_b$, $\kappa_1$, $\kappa_2$). These observations are of key importance for the proposed Reduced Parameter Space techniques.

Equation (16) could be minimized directly using NLLS, which would require in the general case a nonlinear minimization in 6 unknowns and which would be subject to the same limitations as fitting conventional models using NLLS. The proposed Reduced Parameter Space approach, however, may treat the linear ($\kappa_B$, $\kappa_b$, $\kappa_1$, $\kappa_2$) and nonlinear ($\upsilon_1$, $\upsilon_2$) unknowns separately. This is done by first constraining the solution space to only include solutions that minimize the objective function in the linear sense. For the weighted least-squares criterion, this constraint can be implemented by analytically computing the linear parameters ($\kappa_B$, $\kappa_b$, $\kappa_1$, $\kappa_2$) that minimize WSSE as functions of the nonlinear parameters ($\upsilon_1$, $\upsilon_2$) and known or measured quantities—the whole-blood $\{B_j\}$, input function $\{b_j\}$, and measurements $\{\tilde{R}_j\}$.

Taking the derivative with respect to each linear parameter and setting the result to zero, we obtain the linear sub-problem:

$$Ax = b, \quad (17)$$

where:

$$A = \begin{pmatrix} \sum_{j=1}^{T} w_j B_j^2 & \sum_{j=1}^{T} w_j B_j \breve{b}_j & \sum_{j=1}^{T} w_j S_{1,j}(v_1;b) B_j & \sum_{j=1}^{T} w_j S_{2,j}(v_1, v_2;b) B_j \\ \vdots & \sum_{j=1}^{T} w_j \breve{b}_j^2 & \sum_{j=1}^{T} w_j S_{1,j}(v_1;b) \breve{b}_j & \sum_{j=1}^{T} w_j S_{2,j}(v_1, v_2;b) \breve{b}_j \\ \vdots & \vdots & \sum_{j=1}^{T} w_j S_{1,j}^2(v_1;b) & \sum_{j=1}^{T} w_j S_{1,j}(v_1;b) S_{2,j}(v_1, v_2;b) \\ \vdots & \vdots & \vdots & \sum_{j=1}^{T} w_j S_{2,j}^2(v_1, v_2;b) \end{pmatrix},$$

$$x = \begin{pmatrix} \kappa_B \\ \kappa_b \\ \kappa_1 \\ \kappa_2 \end{pmatrix}, \text{ and } b = \begin{pmatrix} \sum_{j=1}^{T} w_j \tilde{R}_j B_j \\ \sum_{j=1}^{T} w_j \tilde{R}_j \breve{b}_j \\ \sum_{j=1}^{T} w_j \tilde{R}_j S_{1,j}(v_1;b) \\ \sum_{j=1}^{T} w_j \tilde{R}_j S_{2,j}(v_1, v_2;b) \end{pmatrix},$$

and "." denotes symmetric matrix elements.

The unconstrained generalized Reduced Parameter Space Reformulation is obtained by applying the separable nonlinear estimation technique by inverting equation (17) and substituting the resultant values for ($\kappa_B$, $\kappa_b$, $\kappa_1$, $\kappa_2$) back into equation (15) to obtain the result shown in equation (18), which is the main theoretical result. The elimination of the linear parameters can be implemented directly per equation (18), or as a two-step process by inverting equation (17) and substituting the results back into equation (15). Both approaches are equivalent for unconstrained estimation, and the latter approach provides a convenient means for imposing non-negativity constraints upon the $\kappa$ s. Referring to equations (8-12), it can be shown that placing non-negativity constraints upon ($\kappa_B$, $\kappa_b$, $\kappa_1$, $\kappa_2$) and ($\upsilon_1$, $\upsilon_2$) effectively places non-negativity constraints upon the individual rate parameters ($K_1$, $k_2$-$k_5$) and $f_B$. Placing additional constraints, e.g. non-zero minimum or maximum values on rate parameters, is likewise workable but involves somewhat more complexity.

Notably, the reformulated model of equation (18) contains only two free parameters ($\upsilon_1$, $\upsilon_2$) for the generalized case. More specifically, the Reduced Parameter Space Reformulation reduces the dimensionality of 1K-5K serial compartment models fitting space as:

1K: Analytical solution (0 free parameters)
2K: One free parameter ($\upsilon_1$)
3K: One free parameter ($\upsilon_1$)
4K: Two free parameters ($\upsilon_1$, $\upsilon_2$)
5K: Two free parameters ($\upsilon_1$, $\upsilon_2$)

Unconstrained Generalized Reduced Parameter Space Reformulation $$\hat{R}_j = \left( \begin{pmatrix} \sum_{j=1}^T w_j B_j^2 & \sum_{j=1}^T w_j B_j \breve{b}_j & \sum_{j=1}^T w_j S_{1,j}(v_1;b) B_j & \sum_{j=1}^T w_j S_{2,j}(v_1,v_2;b) B_j \\ \vdots & \sum_{j=1}^T w_j \breve{b}_j^2 & \sum_{j=1}^T w_j S_{1,j}(v_1;b) \breve{b}_j & \sum_{j=1}^T w_j S_{2,j}(v_1,v_2;b) \breve{b}_j \\ \vdots & \vdots & \sum_{j=1}^T w_j S_{1,j}^2(v_1;b) & \sum_{j=1}^T w_j S_{1,j}(v_1;b) S_{2,j}(v_1,v_2;b) \\ \vdots & \vdots & \vdots & \sum_{j=1}^T w_j S_{2,j}^2(v_1,v_2;b) \end{pmatrix}^{-1} \begin{pmatrix} \sum_{j=1}^T w_j \tilde{R}_j B_j \\ \sum_{j=1}^T w_j \tilde{R}_j \breve{b}_j \\ \sum_{j=1}^T w_j \tilde{R}_j S_{1,j}(v_1;b) \\ \sum_{j=1}^T w_j \tilde{R}_j S_{2,j}(v_1,v_2;b) \end{pmatrix} \right)^T \quad (18)$$

$$\begin{pmatrix} B_j \\ \breve{b}_j \\ S_{1,j}(v_1;b) \\ S_{2,j}(v_1,v_2;b) \end{pmatrix}$$

The application to the 1K model is trivial and included for completeness. Note that application of the separable nonlinear least squares technique to the conventional formulation of the 3K model would result in 2 free nonlinear parameters ($k_2$ and $k_3$). Similarly, one would obtain 3 ($k_2$-$k_4$) and 4 ($k_2$-$k_5$) free nonlinear parameters for the 4K and 5K models, respectively. The proposed Reduced Parameter Space Reformulation, however, reduces the dimensionality to only 1 or 2 unknowns as listed above, maximizing the benefit of the separable nonlinear least squares approach.

The Reduced Parameter Space Reformulation still presents a nonlinear fitting problem (aside from the trivial 1K case); however, the dimensionality of the fit is greatly reduced, markedly simplifying the problem and making exhaustive search computationally feasible. Once the best-fit for the nonlinear unknowns ($\upsilon_1, \upsilon_2$) is obtained, the results can be used to directly compute the individual rate parameters ($K_1$, $k_2$-$k_5$).

Recovery of the Original (Un-Reformulated) Model Parameters

After completing the fit, the individual rate parameters $K_1$, $k_2$-$k_5$, as well as $f_B$, are easily calculated from the best-fit parameters $\kappa_B$, $\kappa_b$, $\kappa_1$, $\kappa_2$, $\upsilon_1$ and $\upsilon_2$. The calculation does merit some discussion of parameter estimability, however. We begin by providing the conversions for the 1K-5K serial compartment models. In all cases $f_B = \kappa_B$. When macro parameters such as the volume of distribution or net uptake are desired, they can either be computed using the individual rate parameters, or more directly in some cases (e.g., the net uptake parameter for the 3K model is more directly calculated as $K_{net}^{(3K)} = \kappa_b^{(3K)}/(1-f_B)$).

1K Model: (19)

$$K_1 = \frac{\kappa_1^{(1K)}}{(1-f_B)}$$

2K Model: (20)

$$K_1 = \frac{\kappa_1^{(2K)}}{(1-f_B)} \text{ and } k_2 = v_1^{(2K)}$$

3K Model: (21)

$$K_1 = \frac{\kappa_b^{(3K)} + \kappa_1^{(3K)}}{(1-f_B)}, \; k_2 = \frac{\kappa_1^{(3K)} v_1^{(3K)}}{\kappa_b^{(3K)} + \kappa_1^{(3K)}}, \text{ and } k_3 = \frac{\kappa_b^{(3K)} v_1^{(3K)}}{\kappa_b^{(3K)} + \kappa_1^{(3K)}}$$

-continued

4K Model: (22)

$$K_1 = \frac{\kappa_1^{(4K)}}{(1-f_B)},$$

$$k_2 = \frac{(\kappa_1^{(4K)} - \kappa_2^{(4K)})v_1^{(4K)} + \kappa_2^{(4K)}v_2^{(4K)}}{\kappa_1^{(4K)}},$$

$$k_3 = \frac{\kappa_2^{(4K)}(\kappa_1^{(4K)} - \kappa_2^{(4K)})(v_2^{(4K)} - v_1^{(4K)})^2}{\kappa_1^{(4K)}[(\kappa_1^{(4K)} - \kappa_2^{(4K)})v_1^{(4K)} + \kappa_2^{(4K)}v_2^{(4K)}]}, \text{ and}$$

$$k_4 = \frac{\kappa_1^{(4K)}v_1^{(4K)}v_2^{(4K)}}{(\kappa_1^{(4K)} - \kappa_2^{(4K)})v_1^{(4K)} + \kappa_2^{(4K)}v_2^{(4K)}}.$$

5K Model:

$$K_1 = \frac{\kappa_b^{(5K)} + \kappa_1^{(5K)}}{(1-f_B)},$$

$$k_2 = \frac{(\kappa_1^{(5K)} - \kappa_2^{(5K)})v_1^{(5K)} + \kappa_2^{(5K)}v_2^{(5K)}}{\kappa_b^{(5K)} + \kappa_1^{(5K)}},$$

$$k_3 = \left\{ \frac{(\kappa_2^{(5K)})(v_1^{(5K)} - v_2^{(5K)}) + \kappa_b^{(5K)}v_1^{(5K)}}{(\kappa_b^{(5K)} + \kappa_1^{(5K)})} + \frac{\kappa_2^{(5K)}v_2^{(5K)}(v_2^{(5K)} - v_1^{(5K)})}{(\kappa_1^{(5K)} - \kappa_2^{(5K)})v_1^{(5K)} + \kappa_2^{(5K)}v_2^{(5K)}} \right\},$$

$$k_4 = \frac{\kappa_1^{(5K)}v_1^{(5K)}v_2^{(5K)}}{(\kappa_1^{(5K)} - \kappa_2^{(5K)})v_1^{(5K)} + \kappa_2^{(5K)}v_2^{(5K)}} - \frac{\kappa_b^{(5K)}v_1^{(5K)}v_2^{(5K)}}{k_3(\kappa_b^{(5K)} + \kappa_1^{(5K)})},$$

and $$k_5 = \frac{\kappa_b^{(5K)}v_1^{(5K)}v_2^{(5K)}}{k_3(\kappa_b^{(5K)} + \kappa_1^{(5K)})}. \tag{23}$$

The above equations provide one-to-one correspondence between any set of Reduced Parameter Space variables and a set of conventional rate parameters, provided that divide-by-zero singularities are not encountered. Under the assumption that a non-negativity constraint has been imposed on all parameters $\kappa_B$, $\kappa_b$, $\kappa_1$, $\kappa_2$, $v_1$ and $v_2$ during fitting, inspection of equations (19-23), along with the modeling equations (8-12), reveals that such singularities generally equate to model simplifications to fewer parameters (where the higher-order parameters are undefined). For example, consider the potential singularity of $f_B=1.0$, affecting all $K_1$ calculations. If the best-fit value of $f_B$ is 1.0, this means the best-fit time-activity curve is pure whole-blood and there is no extravascular tissue uptake. In that case, $K_1$ is zero and all higher-order rate parameters ($k_2$-$k_5$) are undefined and not meaningful (one could consider this a "0K" model).

As another example, consider the cases for the 4K model in which one or more of the denominators could be zero. This could occur when either $\kappa_1^{(4K)}=0$ or the quantity $(\kappa_1^{(4K)}-\kappa_2^{(4K)})\,v_1+\kappa_2^{(4K)}v_2=0$. The former again gives the case where $K_1$ is zero and corresponds to model simplification to the "0K" model. In depth examination of the latter case, however, reveals instances where best-fit κs may arise that are non-negative but give rise to negative individual rate parameters. Addition of the constraint $\kappa_2<\kappa_1$ for both the 4K and 5K models was found to constrain the solution space to include only valid compartment models (e.g. models with real and non-negative rate constants). The need for additional constraints may arise in the application of Reduced Parameter Space formulations to particular kinetic modeling applications in order to ensure valid results given the constraints of the particular problem.

Examples, Evaluation Methods and Results

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

The proposed Reduced Parameter Space Reformulation greatly simplifies the nonlinear fitting problem for kinetic modeling by reducing the dimensionality of the fits as described above. The proposed technique has been evaluated by (1) demonstrating that the conventional and reformulated modeling equations provide identical time-activity curves for the same rate parameters; (2) verifying that both formulations provide the same best-fit global minimum (which requires application of fitting algorithms that attain the true global minimum); (3) further exploring the merits of the reformulated equations by characterizing the resultant 1- and 2-dimensional objective functions; and (4) studying exhaustive search fits using the reformulated equations and characterizing the CPU time required. Together, these tests gauge the value of the proposed Reduced Parameter Space Reformulation and form the basis for future application of the technique to specific modeling tasks using the exhaustive search algorithm. The emphasis of this evaluation is focused on 2K, 3K, and 4K serial compartment models, as these represent the most commonly used compartment models in dynamic PET imaging and cover both 1D (3K) and 2D (4K) Reduced Parameter Space solution equations.

Simulation of Time-Activity Curves

A set of twenty-four typical input functions and whole-blood curves were selected from dynamic PET exams using $^{15}$O-water (2K model), $^{18}$F-fluorodeoxyglucose (FDG; 3K model), and $^{11}$C-acetate (4K model) in patients with malignant solid tumors at our institution. Representative rate parameters ($K_1$, $k_2$-$k_4$) and vascular fractions $f_B$ were also selected based upon conventional fits of 2K-4K compartment models to time-activity curves for various regions-of-interest (ROIs) drawn on the dynamic PET images. The input functions and rate parameter ranges were used to simulate populations of 200-1,000 time-activity curves each for the 2K, 3K, and 4K models using the conventional model formulations. The number of curves in each population was heuristically selected to include enough data points such that "outlier" points (representing best-fit differences between the Reduced Parameter Space and conventional model fits) presented themselves for study. Progressive temporal sampling schemes were used, for example: 18×10 s, 6×20 s, 4×30 s, 5×60 s, 5×120 s, 4×300 s, 3×600 s for a total duration of 72 m for the $^{18}$F 3K model simulations.

Noise-free curves were first simulated for each case. Statistical noise was then added using a noise model that approximates the noise characteristics of iteratively reconstructed PET images. Here, Gaussian deviates were simulated for each datapoint with variance inversely proportional to the time-frame durations, and scaled to five different noise levels. When a noisy sample went negative, however, the absolute value was used—providing an asymmetric non-negative distribution roughly approximating the statistical distribution of iteratively reconstructed PET values. The resulting noisy curves had Gaussian-like non-negative statistics that varied with time-frame duration, providing more realistic test cases than simulating curves that were consistent with either Gaussian or Poisson noise. Note that this noise model is inconsistent with the L2-norm criterion typically used in model fitting (which essentially assumes a Gaussian noise model); however, such inconsistency is a real and present challenge for actual dynamic PET data. Five different noise levels were used, covering the approximate range encountered in the dynamic PET datasets—ranging from high noise in individual voxels to lower noise curves representative of larger tumor ROIs.

Reduced Parameter Space Fits with Exhaustive Search

The dimensionality of the Reduced Parameter Space Reformulation—only one or two free parameters for 2K-3K and 4K-5K compartment models, respectively—is small enough that the entire solution space (within appropriate parameter ranges) can be exhaustively searched to an arbitrary precision with a reasonable amount of computational effort. While such brute-force exhaustive search is slower than "intelligent" minimization techniques such as gradient-descent-type algorithms, exhaustive search guarantees identification of the global minimum to within the selected search precision and parameter ranges. As such, exhaustive search provides the most robust fit for the given data, weights, and input functions. Aside from the specified parameter ranges and search precision, exhaustive search is completely independent of initial conditions, does not depend on the number of iterations or other convergence effects, and likewise avoids any other possible differences between individual minimization algorithms. These properties make exhaustive search ideal for studying the theoretical Reduced Parameter Space formulations in comparison with conventional compartment modeling formulations for fitting time-activity curves. Furthermore, exhaustive search is fast enough with the Reduced Parameter Space formulations to provide rapid and robust fits for routine use.

It is noted, however, that gradient-type algorithms may also be utilized. Such algorithms may include the Levenberg-Marquardt algorithm, steepest descent, inverse Hessian, Newton-Raphson, and the like. Embodiments which have utilized a Levenberg-Marquardt algorithm on curves from dynamic PET imaging data have provided good fit results while utilizing far less iterations with the reformulated model over a conventional model (e.g. 50-90 percent fewer iterations). It is noted that gradient-type algorithms may provide advantages over exhaustive-search type methods because they are faster and do not need to sample every possible solution. However, exhaustive methods may provide more accurate results. It is appreciated that the use and effectiveness of any particular algorithm will be dependent on the particular application of the described methods.

In this example, we implemented exhaustive search routines in C for the Reduced Parameter Space Reformulation of equation (18) for 1K-5K compartment models. The routines loop over $\upsilon_1$ from 0.0 to 2.0 min$^{-1}$ in 1000 steps, sampling $\upsilon_1$ at a precision of 0.002 min$^{-1}$. For the 4K and 5K models, a nested loop over $\upsilon_2$ was likewise included for each value of $\upsilon_1$. Recalling that $\upsilon_2$ should be constrained less than $\upsilon_1$ in order for the Reduced Parameter Space formulation to represent a valid compartment model, this inner loop ranged from 0.0 up to the current value of $\upsilon_1$ in steps of 0.002 min$^{-1}$. This resulted in 1,000 total steps for the 2K-3K models, and ~500,000 steps for the 4K-5K models. For comparison, consider that exhaustive search with conventional compartment model formulations would require $10^9$, $10^{12}$, and $10^{15}$ steps for 2K, 3K, and 4K models, respectively—becoming computationally intractable.

Characterization of Reduced Parameter Space WSSE Objective Functions

Given the reduction in the number of free parameters offered by the Reduced Parameter Space formulations, the objective functions reside within 1D (2K-3K models) or 2D (4K-5K models) solution spaces. Thus, they can be plotted and analyzed much more easily than conventional objective functions in 3-6 dimensions. Using the exhaustive search routines just described, the WSSE objective functions were characterized for a number of noisy 3K and 4K time-activity curves by storing and plotting the WSSE at each value of $\upsilon_1$ (3K) or $\upsilon_1$, $\upsilon_2$ (4K). The resulting objective functions were analyzed for the presence/absence of local minima or other confounding structures that could affect the performance of curve fits using the Reduced Parameter Space formulations with various minimization algorithms.

Characterization of Global Minimums for Both Conventional and Reduced Parameter Space Formulations In order for the Reduced Parameter Space Reformulation to be a viable alternative for kinetic modeling, the reformulated modeling equations should provide the same, or substantially similar, global minimum and best-fit rate parameters as the conventional model equations. In order to perform this study, fits to both model formulations were attempted to be obtained in order to reach the true global minimums. While an "intelligent" minimization algorithm such as Levenberg-Marquardt could have been used, such algorithms are sensitive to initial conditions, finding the closest local minimum, and cannot guarantee identification of the true global minimum. No such problem arises for the Reduced Parameter Space fits using the exhaustive search algorithm, as this algorithm provides identification of the true global minimum to within the parameter ranges and search precision specified.

To overcome these shortcomings, a simulated annealing algorithm was selected for the conventional model fits. As implemented, the simulated annealing algorithm was independent of starting conditions (aside from the set parameter ranges) and included means for escaping local minima and progressing toward the true global minimum provided that enough iterations and a slow enough relaxation schedule were used. Progressively simulated annealing with $10^4$ to $10^8$ iterations were applied, increasing the number of iterations by 10× each step and observing the number of cases in each population where the best-fit solution did not change versus those that continued moving toward a better fit. While this approach cannot truly guarantee that the true global minimum was reached for all fits (only exhaustive search could so guarantee), it did allow visualization of the progression of the population of fits toward the true global minima as discussed herein.

Figure 3:
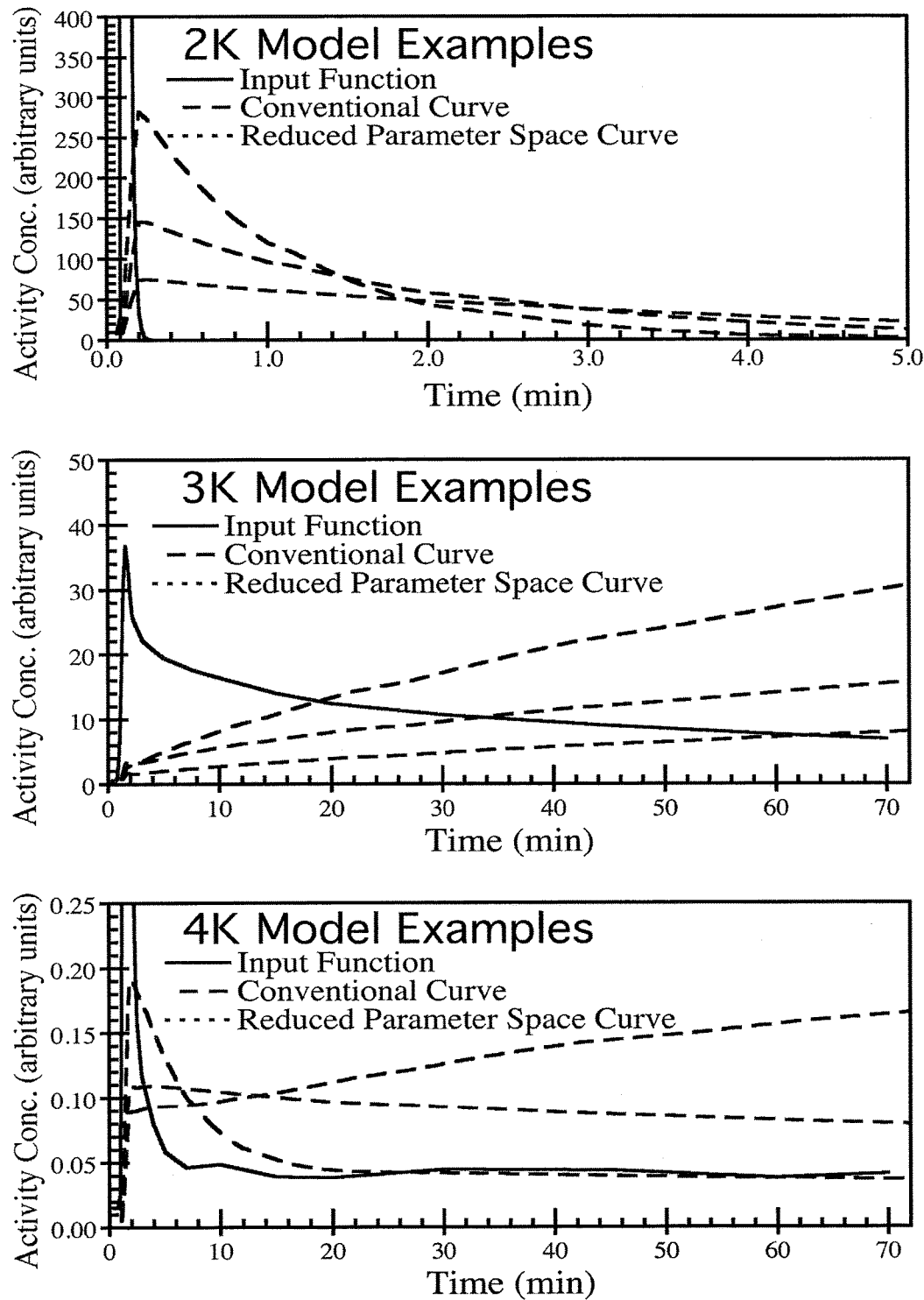
FIG. 3 shows example time-activity curves for 2K (based on $^{15}$O-water), 3K (based on $^{18}$F-FDG), and 4K (based on $^{11}$C-acetate) compartment models.

Verification that the Conventional and Reformulated Equations Provide the Same Time-Activity Curves FIG. 3 shows example time-activity curves for 2K (based on $^{15}$O-water), 3K (based on $^{18}$F-FDG), and 4K (based on $^{11}$C-acetate) compartment models. For each model, three representative sets of rate parameters were selected and curves were simulated using both the conventional model formulations per equations (9-11), and with the Reduced Parameter Space Reformulation of equation (18). For the latter case, the values of $\kappa_B$, $\kappa_b$, $\kappa_1$, $\kappa_2$, $\upsilon_1$, and $\upsilon_2$ were computed from the conventional rate parameters according to the conversions described above. The curves for each case were identical up to the numerical precision of the computer, confirming that the Reduced Parameter Space Reformulation correctly represents valid compartment models for these data.

Characterization of Objective Functions

Figure 4:
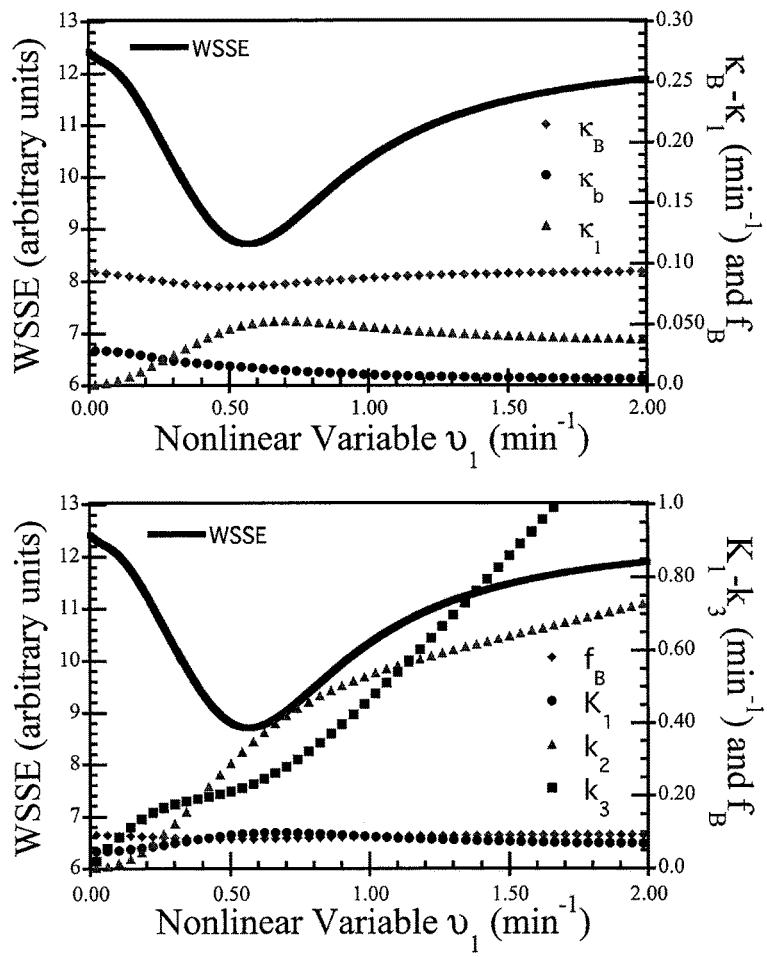
FIG. 4 shows a representative WSSE objective function for a 3K compartment model fit to a noisy time-activity curve modeled on dynamic FDG PET tumor imaging.

The Reduced Parameter Space Reformulation reduces the dimensionality of the nonlinear kinetic model fitting problem to only one free parameter for 2K-3K compartment models, and to only two free parameters for 4K-5K compartment models. The resultant 1D and 2D objective functions can be plotted and analyzed more easily than conventional objective functions in 3-6 dimensions. FIG. 4 shows a representative WSSE objective function for a 3K compartment model fit to a noisy time-activity curve modeled on dynamic FDG PET tumor imaging. The objective function is well-behaved, having a single well-defined minimum and no other confounding structures such as local minima or shelves. The plot also shows how the values of $\kappa_B$, $\kappa_b$, and $\kappa_1$ vary as functions of $\upsilon_1$ to keep WSSE minimized according to equation (17); the corresponding values of $f_B$ and the conventional rate parameters are also shown in the lower plot for comparison.

Figure 5:
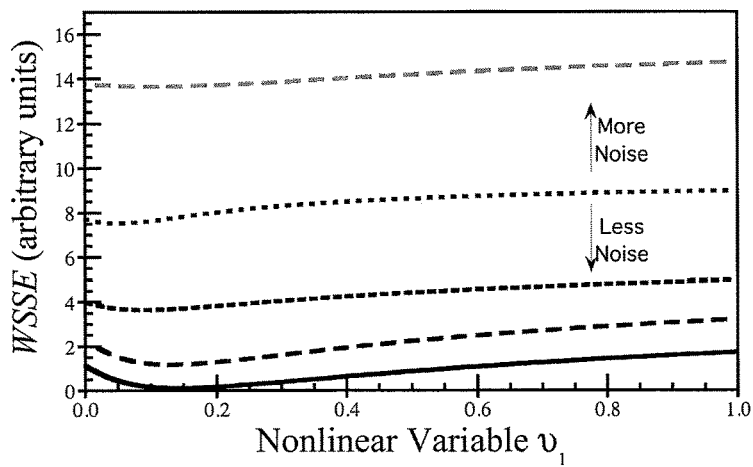
FIG. 5 shows example Reduced Parameter Space WSSE objective functions for another representative 3K model curve at five different noise levels.

FIG. 5 shows example Reduced Parameter Space WSSE objective functions for another representative 3K model curve at five different noise levels. The minimum is deepest for the lowest noise curve, and becomes shallower with increasing noise—consistent with the observation that the best-fit parameters will have greater statistical variability for noisier data. Only a single minimum was present for each case and the objective function remained well-behaved for all noise levels studied.

Figure 6:
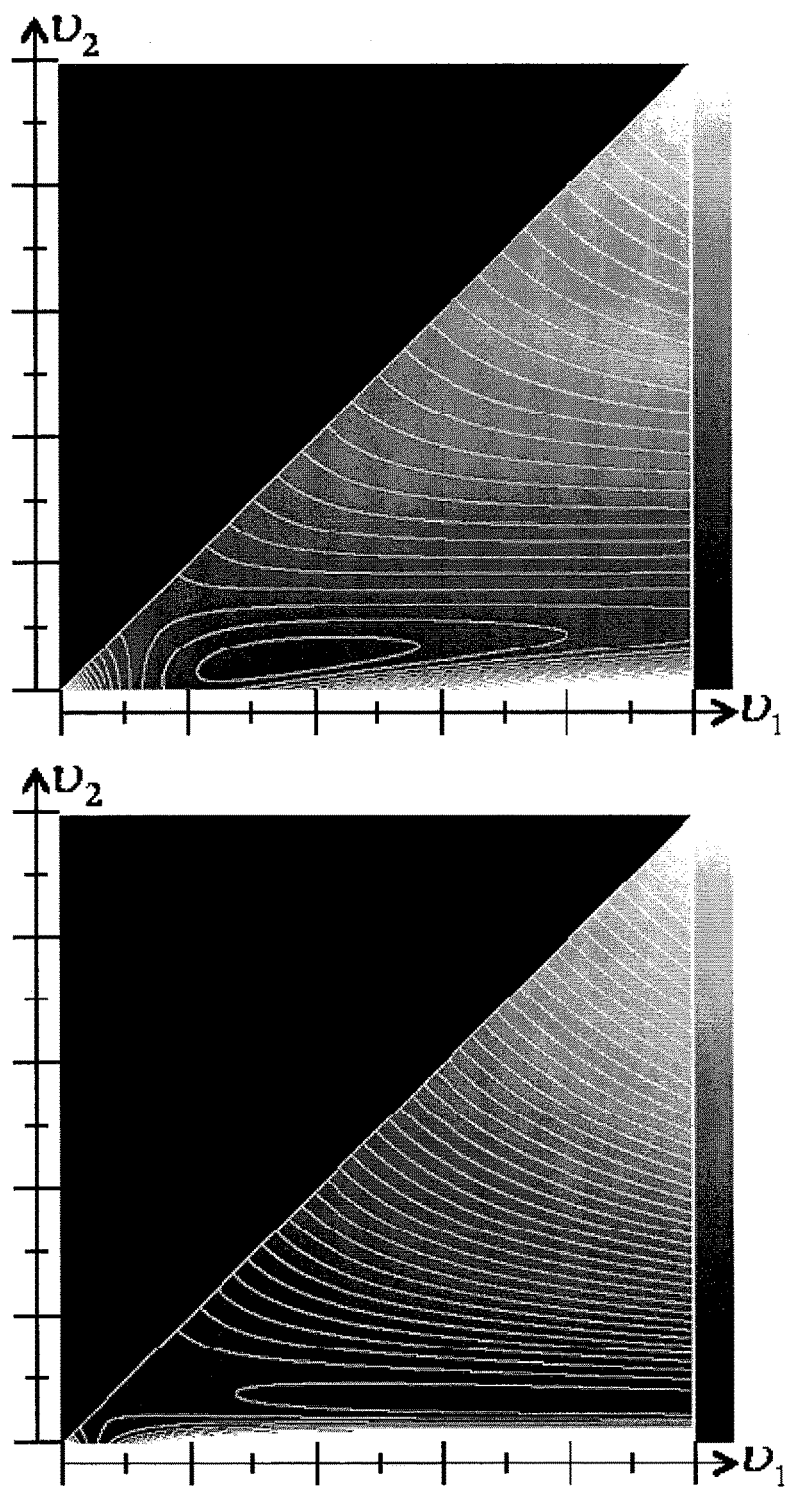
FIG. 6 shows representative objective functions in two dimensions for the 4K compartment model using the Reduced Parameter Space Reformulation.

Representative objective functions in two dimensions for the 4K compartment model using the Reduced Parameter Space Reformulation are provided in FIG. 6. Here the reformulation has two nonlinear unknowns, $\upsilon_1$ and $\upsilon_2$, both of which are constrained to be non-negative, and further the search was constrained to values $\upsilon_2 < \upsilon_1$ in order to limit the solution space to regions that represent valid compartment models. The objective functions were again generally well-behaved, with only a single minimum, although some complexity was present for lower values of $\upsilon_1$ that may be considered a "side valley". These curvatures in the objective function arise from imaginary "poles" in the excluded regions $\upsilon_2 > \upsilon_1$ and $\upsilon_2 < 0$ (where the Reduced Parameter Space Reformulation does not represent value compartment models, and would give rise to rate parameters with either negative or imaginary values).

Overall, we have generated objective functions for hundreds of 2K-4K models at various noise levels and analyzed them using a simple computer algorithm which steps through the full solution space and checks for local minima. In all cases, only a single minimum was present within the space of valid solutions (though local minima do exist outside of the valid region; e.g. for $\upsilon_2 > \upsilon_1$ or $\upsilon_2 < 0$), and no local minima or "shelves" with zero slope were encountered. Hence, the Reduced Parameter Space Reformulation objective functions are generally well-behaved and well-suited for minimization via gradient-descent-type minimization algorithms.

Figure 7:
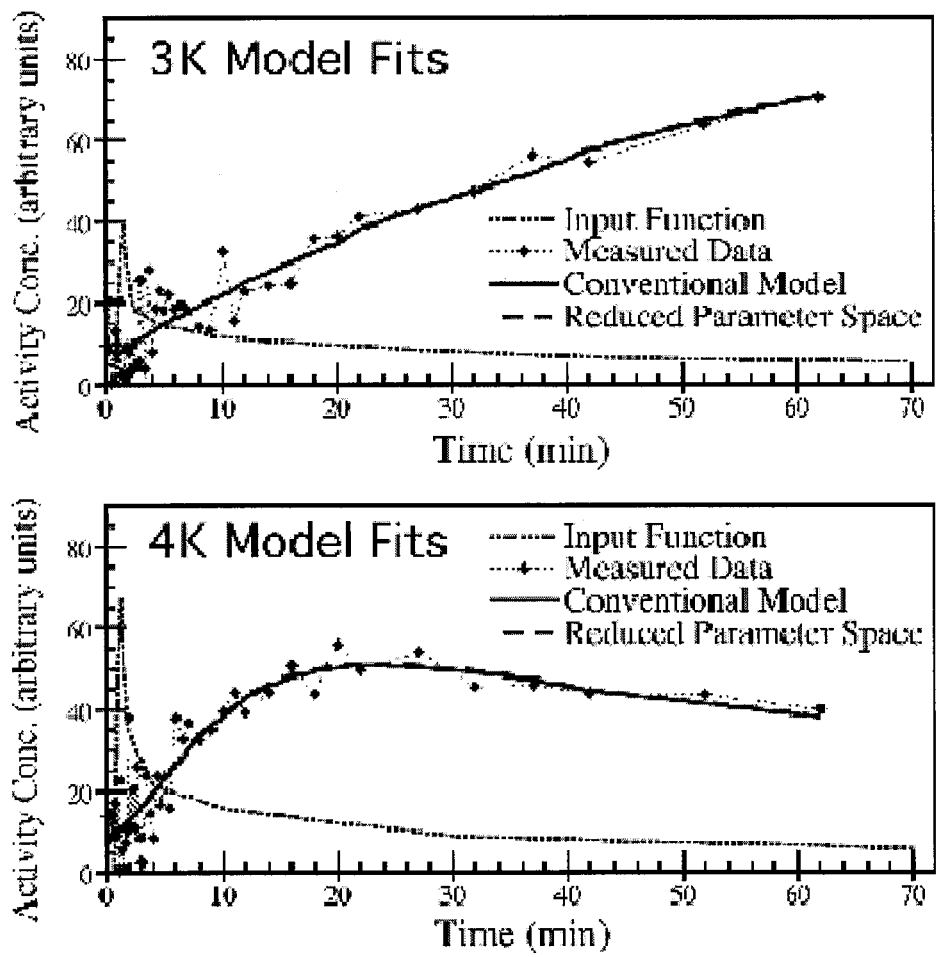
FIG. 7 provides example noisy time-activity curves and fits with both the conventional and Reduced Parameter Space model formulations.

Verification that the Conventional and Reformulated Model Equations have the Same Global Minimum FIG. 7 provides example noisy time-activity curves and fits with both the conventional and Reduced Parameter Space model formulations. The plots also illustrate representative levels of statistical noise that were used for the noisy population studies. Populations of 200-1,000 noisy time-activity curves representative of dynamic PET tumor imaging with $^{15}$O-water (2K model), $^{18}$F-FDG (3K model), and $^{11}$C-acetate (4K model) were simulated using methods described above. Each noisy curve was fit to the Reduced Parameter Space model formulations using the exhaustive search algorithm with non-negativity constraints. The curves were also fit to the conventional model formulations using simulated annealing, where the fits were repeated using $10^4$ to $10^8$ iterations progressively in 10× increments.

Figure 8:
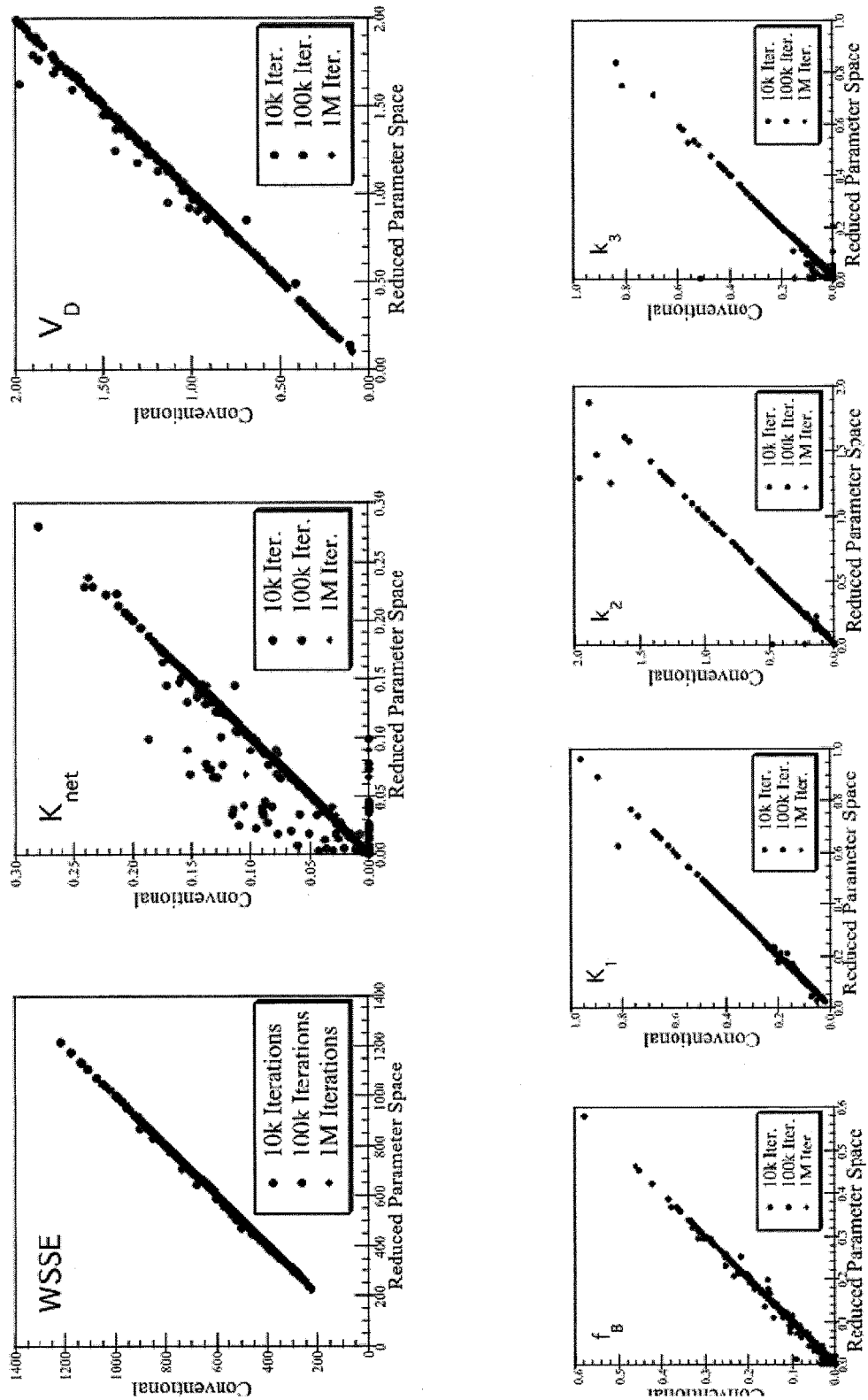
FIG. 8 shows scatter plots of the best-fit WSSE and rate parameters for the 3K model comparing conventional model fit results to the Reduced Parameter Space formulation fits.
Figure 9:
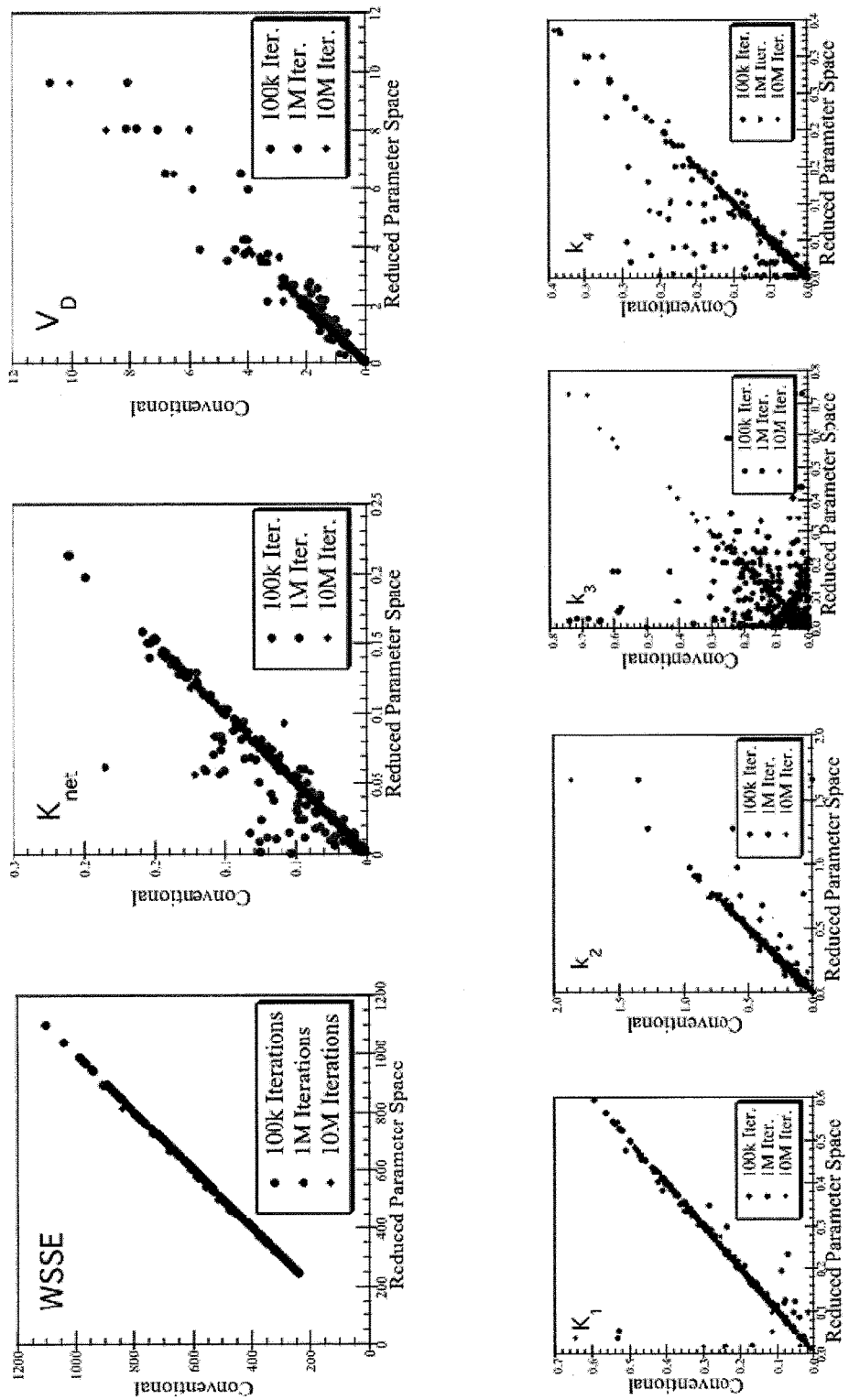
FIG. 9 shows analogous results for the 4K model.

FIG. 8 shows scatter plots of the best-fit WSSE and rate parameters for the 3K model comparing conventional model fit results to the Reduced Parameter Space formulation fits. Analogous results for the 4K model are provided in FIG. 9. These figures also include results for the macroparameters $K_{net}$ and $V_D$ (which may have varying physiologic interpretations for the different models and particular applications, but are generally considered easier to estimate than the individual rate parameters). In all cases the exhaustive search fits produced equal or lower WSSE than the conventional simulated annealing fits to within the numerical precision of the exhaustive search (approx. 1 part in $10^{-3}$). This result is consistent with exhaustive search identifying the true global minimum to within the selected precision for all fits. The conventional model fits with simulated annealing progressively approached the Reduced Parameter Space exhaustive search results, further confirming that these fits were indeed the best-fit cases, and that both model formulations provide the same best-fit global minimums.

Linear regression analysis between the conventional (maximum number of iterations) and Reduced Parameter Space fits revealed slopes of $1.000 \pm 0.001$ and Pearson correlation coefficients greater than 0.999 for all individual rate parameters and macro parameters. These results confirm that both the conventional models and Reduced Parameter Space formulations provided identical best-fit results across these populations of curves to within the precision of the search. Small differences on the order of $10^{-4}$ were observed in the final rate parameters, consistent with a search precision on the order of $10^{-3}$ for Reduced Parameter Space (note that this precision is applicable to the nonlinear parameters $\upsilon_1$ and $\upsilon_2$; calculation of the linear ($\kappa$) parameters and then conversion to kinetic rate parameters $K_1$-$k_4$ were computed at full floating point double-precision).

Computational Cost for Exhaustive Search Algorithm

The CPU time required to perform each of the fits for the population results data were recorded to provide a measure of the computational cost of both the Reduced Parameter Space exhaustive search and conventional simulated annealing fits. It is noted that both the conventional and Reduced Parameter Space fits were performed with algorithms designed to robustly attain the true global minimum, rather than using fast minimization algorithms (such as Levenberg-Marquardt) designed to rapidly find the closest local minimum. Both model formulations could also be implemented with fast iterative algorithms, greatly reducing the computational cost but also adding the complexity of needing to identify appropriate initial conditions, convergence criteria, and mechanisms for escaping local minima or shallow valleys (at least for the conventional model formulation, as no such confounding structures have been observed in the Reduced Parameter Space fitting spaces). Both the conventional models with simulated annealing and Reduced Parameter Space formulations with exhaustive search were implemented as subroutine options in the same C code, with identical attention to optimizing the code for computational efficiency.

Table II shows the CPU times for fitting a single noisy time-activity curve with 2K, 3K, and 4K models using both the conventional and Reduced Parameter Space algorithms. Times were computed for single-threaded code run on a 2.80 GHz Intel Xeon workstation, and no acceleration via multi-threading has yet been implemented. Fitting times ranged from tenths of a second to several minutes for the conventional model fits with simulated annealing, depending on the number of iterations selected. Recalling the convergence effects discussed in the previous section, the higher numbers of iterations were necessary to provide the most robust fits for all curves; these resulted in average fitting times of 2.2 s, 19.7 s, and 238 s for the 2K, 3K, and 4K models, respectively. In comparison, the Reduced Parameter Space $$\hat{R}_j = \left( \underbrace{\begin{pmatrix} \sum_{j=1}^{T} w_j B_j^2 & \sum_{j=1}^{T} w_j B_j \breve{b}_j & \sum_{j=1}^{T} w_j S_{1,j}(v_1;b) B_j \\ \vdots & \sum_{j=1}^{T} w_j \breve{b}_j^2 & \sum_{j=1}^{T} w_j S_{1,j}(v_1;b) \breve{b}_j \\ \vdots & \vdots & \sum_{j=1}^{T} w_j S_{1,j}^2(v_1;b) \end{pmatrix}^{\dagger}}_{M} \underbrace{\begin{pmatrix} \sum_{j=1}^{T} w_j \tilde{R}_j B_j \\ \sum_{j=1}^{T} w_j \tilde{R}_j \breve{b}_j \\ \sum_{j=1}^{T} w_j \tilde{R}_j S_{1,j}(v_1;b) \end{pmatrix}}_{x} \underbrace{\begin{pmatrix} B_j \\ \breve{b}_j \\ S_{1,j}(v_1;b) \end{pmatrix}}_{y} \right)^T$$

fits with exhaustive search sampled at 1,000 steps for each nonlinear parameter ($v_1$, $v_2$) required 0.01 s for the 2K and 3K models and 1.11 s for the 4K model fits. Fitting times were only moderately increased when implementing non-negativity constraints. These results indicate that the reduced dimensionality of the solution space offered by the Reduced Parameter Space technique provides for very fast and robust fits—up to several orders-of-magnitude faster than the conventional fits used here. Similar benefits are achieved when implementing the fits with gradient-descent type algorithms and optimizing the algorithms for the requirements of specific model fitting problems.

TABLE II

CPU TIMES FOR FITS

| Model | Simulated Annealing (Conventional Formulations) | | Exhaustive Search (Reduced Parameter Space Reformulations) | |
|---|---|---|---|---|
| | No. Iterations | CPU Time(s) | Unconstrained Time(s) | Non-negativity Constraint(s) |
| 2K | $10^3$ | 0.136 ± 0.010 | | |
| | $10^4$ | 0.326 ± 0.022 | 0.0102 | 0.0106 |
| | | | 0.0015 | 0.0025 |
| | $10^5$ | 2.225 ± 0.138 | | |
| 3K | $10^4$ | 0.301 ± 0.048 | | |
| | $10^5$ | 2.227 ± 0.163 | 0.0101 | 0.0105 |
| | | | 0.0009 | 0.0024 |
| | $10^6$ | 19.71 ± 3.17 | | |
| 4K | $10^5$ | 2.849 ± 0.315 | | |
| | $10^6$ | 24.06 ± 4.51 | 1.109 ± 0.183 | 1.119 ± 0.183 |
| | $10^7$ | 238.3 ± 47.4 | | |

Reduced Parameter Space Fits with Levenberg-Marquardt

Fast gradient-descent type iterative fitting algorithms can also be used with the Reduced Parameter Space technique, as illustrated here for the application of the Levenberg-Marquardt (LM) algorithm to fitting a time-activity curve with the 3K compartment model. The Levenberg-Marquardt algorithm is summarized by the following:

Let:

$\nabla$(WSSE)=gradient $\mathcal{H}$(WSSE)=Hessian $\lambda$=non-dimensional factor (note: Numerical Recipes suggests initializing $\lambda$=0.001)

$\delta v_1$=small change in the parameter $v_1$

The Reduced Parameter Space Formulation for 3K modeling is:

Update Equation:

$$v_1^{new} = v_1^{old} + \delta v_1 \text{ where } \delta v_1 = \frac{\nabla(WSSE)}{(1+\lambda)\mathcal{H}(WSSE)}$$

Example Algorithm Steps:
1) Give an initial guess to the unknown parameter $v_1$
2) Compute WSSE at $v_1$: WSSE($v_1$)
3) Pick a modest value $\lambda$=0.001
4) Solve the update equation above for $$\delta v_1: \delta v_1 = \frac{1}{(1+\lambda)}\frac{\nabla(WSSE)}{\mathcal{H}(WSSE)}, \text{ where}$$

$$\nabla(WSSE) = \sum_{j=1}^{T} w_j \left[ \left((M^{\dagger}x)^T y\right)_j - \tilde{R}_j \right] \left[ \frac{\partial}{\partial v_1}\left((M^{\dagger}x)^T y\right)_j \right]$$

$$\mathcal{H}(WSSE) = \sum_{j=1}^{T} w_j \left[ \frac{\partial}{\partial v_1}\left((M^{\dagger}x)^T y\right)_j \right] \left[ \frac{\partial}{\partial v_1}\left((M^{\dagger}x)^T y\right)_j \right]$$

5) Evaluate WSSE at $v_1+\delta v_1$: WSSE($v_1+\delta v_1$)
6) If WSSE($v_1+\delta v_1$)≥WSSE($v_1$), increase $\lambda$ by a factor of 10 and go back to step 5) above
7) If WSSE($v_1+\delta v_1$)<WSSE($v_1$), decrease $\lambda$ by a factor of 10, update the trial solution $v_1 \leftarrow v_1+\delta v_1$
8) Check convergence—stop if converged, else go back to step 5)

The calculation of the gradient and Hessian terms can be computed in a variety of ways when applied to the Reduced Parameter Space Reformulation. Here, the derivatives of the gradient and Hessian are computed with respect to only the nonlinear parameters ($v_1$, $v_2$), as the linear parameters are already constrained (e.g. solved) by the Reduced Parameter space technique. The full gradient and Hessian can be computed directly from equation (18), in which case the linear parameters do not appear in the gradient and Hessian terms. Alternatively, the linear parameters can remain in the equations as per equation (17), in which case the gradient and Hessian can be applied to equation (17) and the resulting expressions will include both the linear and nonlinear model parameters. In this case, the values of the linear parameters for the current values of $\upsilon_1$, $\upsilon_2$ are used when computing the derivatives, and then these values are recomputed after the iterative update in $\upsilon_1$, $\upsilon_2$. The implementation in which the gradient and Hessian are applied to equation (18) is referred to as the "direct" method of constraining the solution space (because the linear parameters are eliminated from the equations), whereas the implementation where the gradient and Hessian are applied to equation (17) and the linear parameters remain is referred to as the "indirect" method of constraining the solution space.

Levenberg-Marquardt fits for the Reduced Parameter Space Reformulation were tested and compared to conventional Levenberg-Marquardt fits on 60 time-activity curves taken from dynamic FDG PET imaging in patients with malignant brain tumors. Since it is well-known that the LM algorithm is sensitive to initial conditions and converges to the nearest local minimum, each fit was repeated 100 times with random initial conditions. In practice, the user would typically inspect each time-activity curve and manually select reasonable initial conditions. However, the objective of this work is to provide fast and robust fitting without any such manual selection of parameters; as such, we characterized the fits using random sets of initial conditions.

In this example, the true best-fit result was determined in 2 ways: (i) by running simulated annealing upon the conventional model formulation with $10^8$ iterations—which randomly exits local minimum and converges toward the true global minimum provided that enough iterations are performed; and (ii) using the exhaustive search algorithm for the Reduced Parameter Space Reformulation. Both of these cases provided identical fits, confirming the true global minimum.

Figure 10:
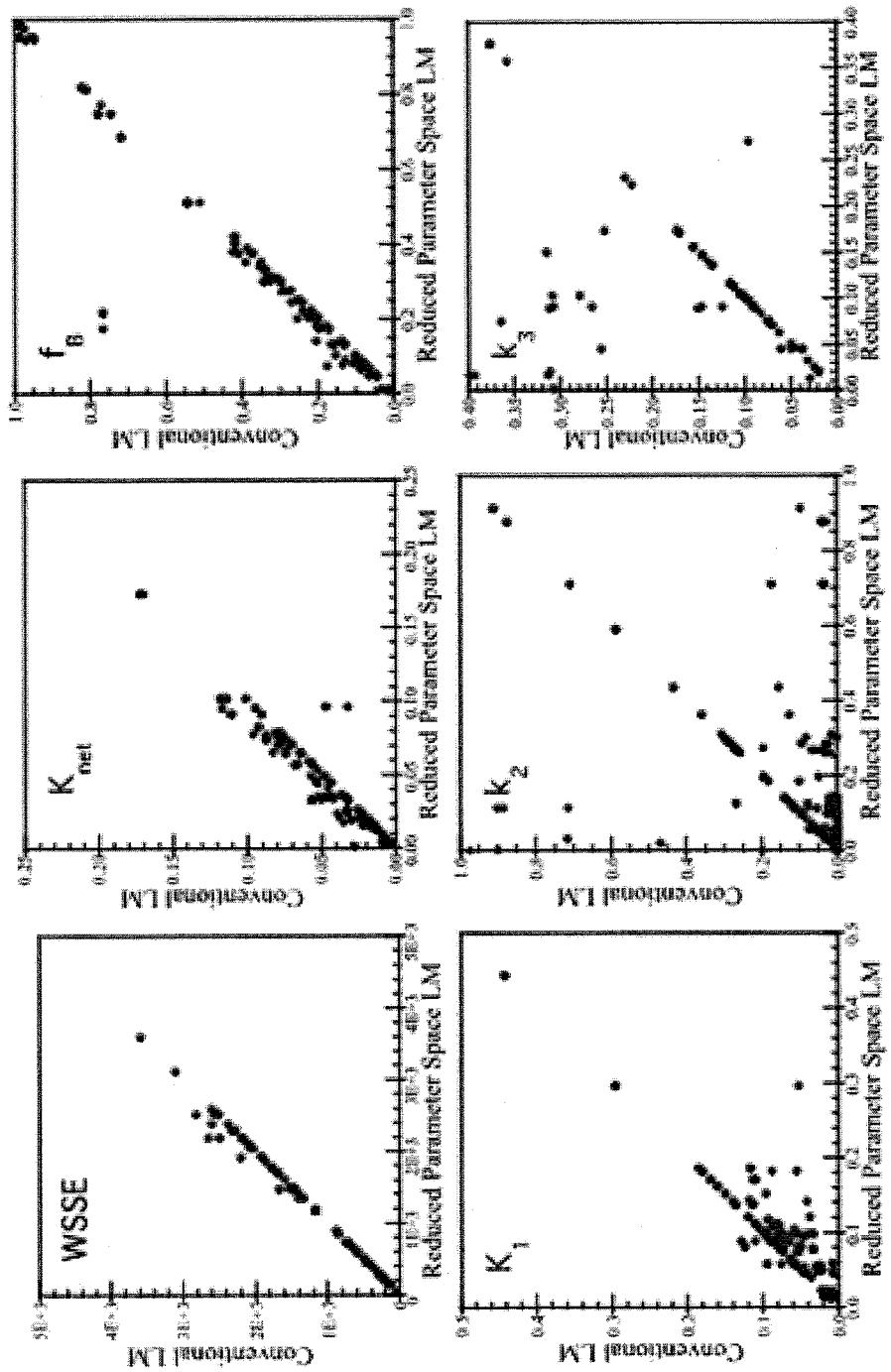
FIG. 10 shows scatter plots comparing the conventional LM fits to the proposed Reduced Parameter Space LM fits.

FIG. 10 shows scatter plots comparing the conventional LM fits to the proposed Reduced Parameter Space LM fits. In this example, 60 time-activity curves were taken from dynamic FDG PET imaging of patients with malignant brain tumors. Each fit was run 100 times with random initial conditions. The conventional LM fits identified the true global minimum in 53.5% of the cases studied, converged to a "good fit" (somewhat different from the true best-fit) in 44.2% of the cases, and failed to converge to a good fit in 2.4% of cases. In contrast, the proposed Reduced Parameter Space LM fits correctly attained the true global minimum in 100% of the cases. Conventional LM averaged 207 iterations (range 12-3,482) to converge, whereas the proposed fits averaged 27 iterations (range 13-73) and required on-avg. 6 ms CPU time.

The application of Levenberg-Marquardt to the Reduced Parameter Space Reformulation provided extremely fast and robust fits. The true global minimum was attained in all cases, whereas conventional model fits were sensitive to initial conditions and converged to local minima for some initial conditions. The reformulated fits converged in avg. 27 iterations, requiring on avg. 0.006 CPU sec. (single-thread) to reach the true global minimum in all cases.

Reduced Parameter Space Fits for Multi-Tracer Kinetic Modeling

The Reduced Parameter Space Kinetic Modeling technique brings even greater advantages when applied to simultaneous multi-tracer compartment modeling, such as arises then imaging more than one tracer at a time with dynamic PET. Parallel multi-tracer compartment modeling involves fitting a model of the form:

$$R^{(Multi)}(t) = f_B B^{(Multi)}(t) + (1-f_B)\sum_{n=1}^{N} C^{(n)}(t; b^{(n)}(t), \{k_i^{(n)}\})$$

where $B^{(Multi)}(t)$ is the total tracer concentration in whole-blood (including all tracers), $b^{(n)}(t)$ is the input function for tracer n, $\{k_i^{(n)}\}$ are the rate parameters for tracer n, and N is the number of tracers present. As written above, $C^{(n)}(t; b^{(n)}(t), \{k_i\})$ is the modeled activity for tracer n in the extravascular tissue compartments.

The reformulated linear and nonlinear parameters for tracer n are noted as $\kappa_i^{(n)}$ and $\upsilon_i^{(n)}$, respectively. The gives rise to the reformulated generalized multi-tracer modeling equation:

$$\hat{R}_j^{(Multi)} = \kappa_B B_j^{(Multi)} + \sum_{n=1}^{N}\left[\sum_i \kappa_i^{(n)} S_{i,j}^{(n)}(\upsilon_i^{(n)}; b^{(n)})\right]$$

This equation can also be written in the form:

$$\hat{R}_j^{(Multi)} = \begin{bmatrix} B_j^{(Multi)} & \{S_{i,j}^{(1)}(\upsilon_i^{(1)}; b^{(1)})\} & \{S_{i,j}^{(2)}(\upsilon_i^{(2)}; b^{(2)})\} & 0 \end{bmatrix}\begin{bmatrix} \kappa_B \\ \{\kappa_i^{(1)}\} \\ \{\kappa_i^{(2)}\} \\ \vdots \end{bmatrix}$$

where the temporal terms $\{S_{i,j}^{(n)}(\upsilon_1^{(n)}; b^{(n)})\}$ for each tracer n consist of either 1 or 2 terms for 1K-5K compartment models.

Constraining the solution space to only include solutions that optimize the objective function in the linear sense per the Reduced Parameter Space modeling technique, one obtains the Multi-Tracer Reduced Parameter Space Reformulation:

$$\hat{R}_j = \left(\begin{bmatrix} [WB]^2 & \{WB\times\text{Tracer}\} & \{WB\times\text{Tracer 2}\} & 0 \\ \vdots & \{\text{Tracer }1^2\} & \{\text{Tracer 1}\times\text{Tracer 2}\} & 0 \\ \vdots & \vdots & \{\text{Tracer }2^2\} & 0 \\ \vdots & \vdots & \vdots & \ddots \end{bmatrix}^{\dagger}\underbrace{\begin{pmatrix} [WB] \\ \{\text{Tracer 1}\} \\ \{\text{Tracer 2}\} \\ \vdots \end{pmatrix}}_{x}\right)^T$$

$$\underbrace{\begin{pmatrix} B_j \\ \{S_{i,j}^{(1)}(\upsilon_i^{(1)}; b^{(1)})\} \\ \{S_{i,j}^{(1)}(\upsilon_i^{(1)}; b^{(1)})\} \\ \vdots \end{pmatrix}}_{y}$$

Notably, this proposed reformulation includes only known quantities and 1-2 nonlinear free parameters ($\upsilon_1^{(n)}$) for each tracer. As a result, the dimensionality of the nonlinear multi-tracer fitting problem is greatly reduced. For example, fitting a dual-tracer 3K+3K model requires a 7-dimensional fit in the conventional formulation ($f_B$ plus $K_1-k_3$ for each tracer), but reduces to only a 2-dimensional nonlinear fit here.

Figure 11:
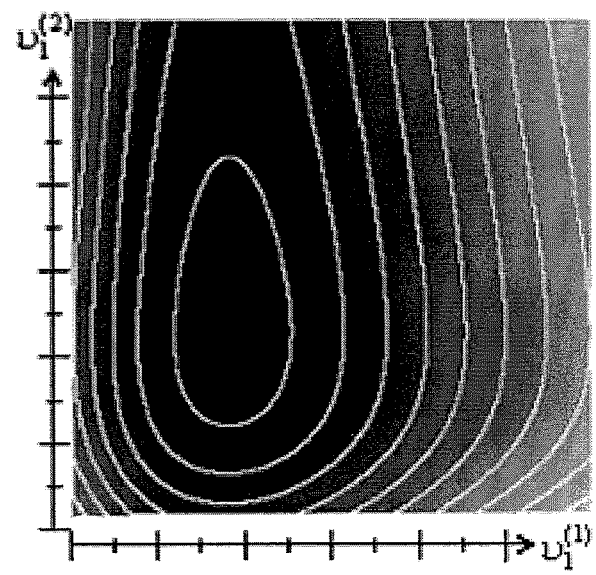
FIG. 11 is an example objective function for Multi-Tracer Reduced Parameter Space Kinetic Modeling for a dual-tracer in accordance with an embodiment of the present application.
Figure 12:
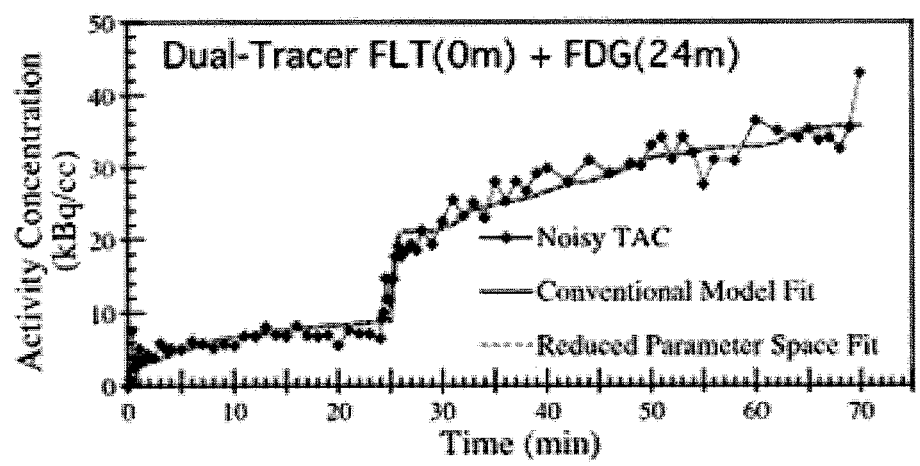
FIG. 12, modeling shows an example dual-tracer objective function and FLT+FDG time-activity curve fit in accordance with the example embodiment of FIG. 11.

FIG. 11 shows an example dual-tracer objective function and FIG. 12 shows an FLT+FDG time-activity curve fit with both conventional parallel compartment modeling and with the proposed Multi-Tracer Reduced Parameter Space Reformulation. The conventional fit was performed using $10^8$ iterations of simulated-annealing, which provides a means for escaping local minima and iterates toward the true global minimum provided enough iterations are performed. The Reduced Parameter Space Fit was performed using $10^3$ steps for each tracer. Both fits produced identical WSSEs and rate parameters to 4 significant digits; however, the conventional fit with simulated annealing required 32 min. whereas the proposed fit took 19.2 sec. In all cases studied, the proposed Reduced Parameter Space Reformulation with exhaustive search correctly identified the true global minimum in under 1 min. CPU time (single-threaded). The proposed Reduced Parameter Space Reformulation provides very fast and robust fits for multi-tracer compartment models, overcoming the limitations of conventional compartment fitting techniques.

In the embodiment of FIGS. 11-12, the conventional fit was run with excessive iterations of simulated annealing in order to ensure a good fit, whereas the Reduced Parameter Space was run with just $10^3$ steps for each tracer. Both fits overlap exactly, demonstrating that the Reduced Parameter Space fit obtained the same solution in a fraction of the fitting time and effort As can be seen, the described Reduced Parameter Space technique for kinetic model fitting provides significant practical and computational advantages over previously implemented methods. Provided below are flow diagrams which illustrate example implementations for carrying out the described methods. It is appreciated that various steps set forth in the following example(s) may be implemented as described, in differing orders, or in some instances certain steps may be omitted. Such modifications would be recognized by one of skill in the art.

Figure 13:
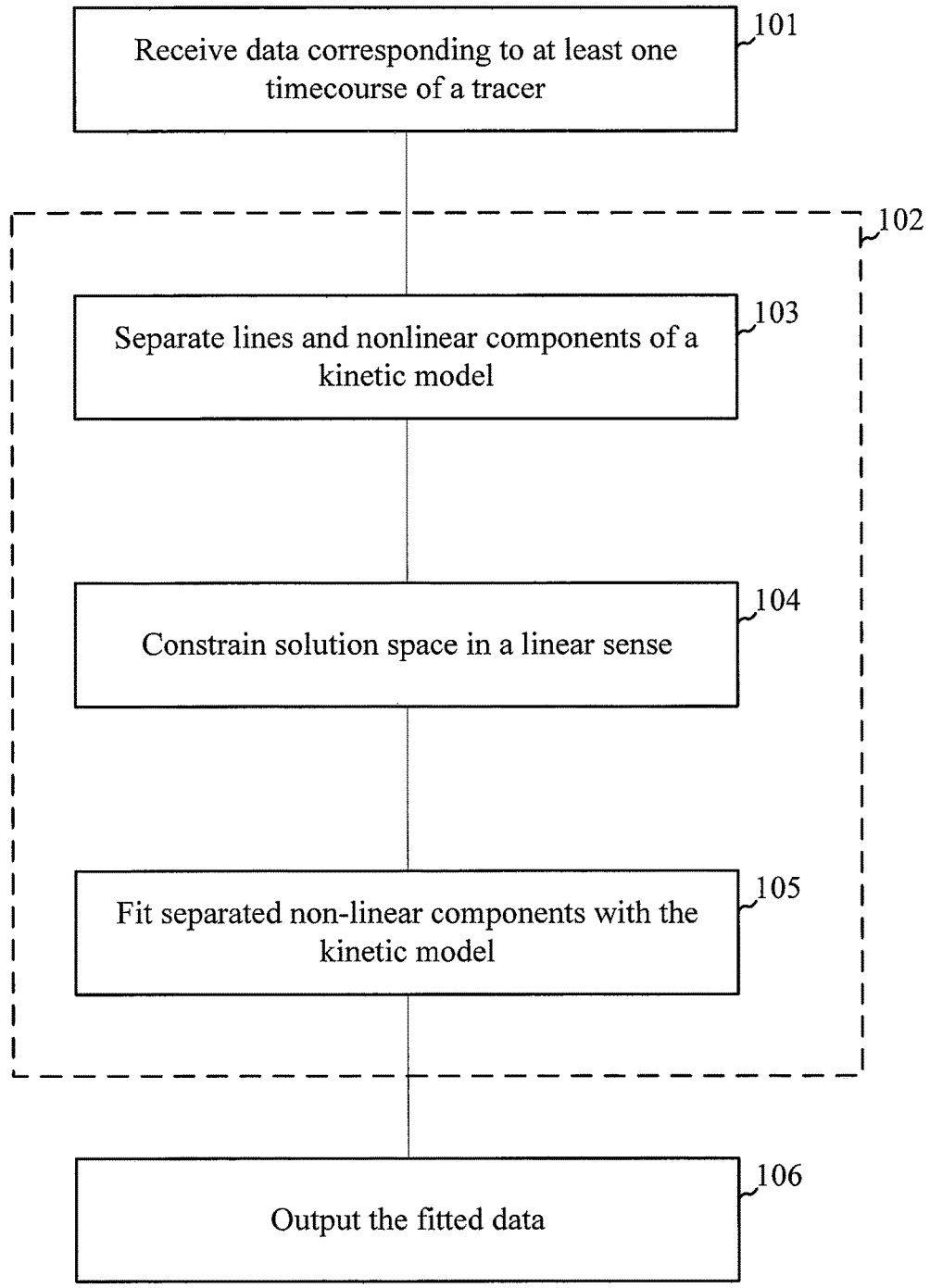
FIG. 13 is a flow chart illustrating an exemplary process for evaluating tracer kinetics in accordance with an embodiment of the present application.

FIG. 13 is a flow chart illustrating an exemplary process 100 for evaluating tracer kinetics in accordance with an embodiment of the present application. Process 100 begins by receiving data corresponding to at least one timecourse of a tracer at block 101. As noted above, a tracer may be any subject that is being modeled over time such as an imaging agent, radiotracer, pharmaceutical, drug, compound, radionuclide, and the like. Data received corresponding to a tracer may come from many different devices dependent upon the particular application implementing the described methods. For example, data corresponding to a tracer may be generated by a medical tomography device such as a PET, SPECT, CT, MRI device, etc. In such embodiments the tracer will often be a radiotracer or radionuclide-type tracer where information regarding the decay of a radioactive substance is being modeled. Further, data corresponding to a tracer may originate from pharmacological studies or methods where, for example, a concentration of a substance or drug within a blood sample is being monitored. It is appreciated that many applications, even non-medical applications, may utilize the described methods. Such methods are regarded to be within the scope of the present application.

It is further noted that embodiments may be utilized in a single-tracer setting or in a multi-tracer setting. The above discussions illustrate many types of tracers, any of which may be utilized in a single-tracer setting. An example of a multi-tracer setting may be found in a circumstance where multi-tracer PET imaging is performed in order to characterize both tumor metabolism and proliferation using two PET tracers in a single scan. As another example, dual-tracer fitting may be required when studying two different neuro-receptors in the brain at the same time.

At block 102, a kinetic model is fitted to the received data. This fitting includes reformulating a kinetic model to separate out linear and non-linear components 103. Such separation may be implemented as described above with respect to the 1K-5K compartment models, or upon other types of models which have both linear nonlinear components. With these components separated, process 100 may then implement fitting methods on the separate components. Such separate implementation allows for improvements in efficiency as simpler methods or different estimation methods may be implemented according to different applications or circumstances between the various components.

With the separated linear components, method 100 constrains the solution space in a linear sense at block 104. Such constraining may be implemented either directly in a single-step, or indirectly over 2 steps. When implemented directly, the linear parameters are completely removed from the modeling equations, but the subsequent modeling equation may become long and involved. When implemented indirectly, the modeling equation is less complex, but the linear parameters must be constrained with additional equations. Both approaches are identical when using the Exhaustive Search fitting algorithm; however, the direct approach may be required to get the best results when using fast iterative gradient-descent type fitting algorithms. As a result of the constraining step at block 104, a fitting solution is derived for the separated linear parameters.

With respect to the separated non-linear parameters, a non-linear algorithm is then utilized to fit the nonlinear component with the kinetic model at block 105. As described above, because the linear and non-linear components are separated a reduced data set is present and varying methods may be utilized to fit the nonlinear component which may have been exceedingly computationally intensive in the absence of such a separation. In one embodiment, applying a non-linear fitting algorithm comprises utilizing an exhaustive search algorithm. Such an exhaustive search algorithm provides accurate results and may be utilized in an efficient manner for a variety of models.

Alternative embodiments may utilize other methods, such as an iterative algorithm, to fit the nonlinear component with the kinetic model. In an iterative algorithm an initial guess for the nonlinear parameters is made, and then the algorithm iteratively updates the parameter values, moving toward the best-fit solution. Such iterative algorithms may be much faster than exhaustive search because they use feedback from the current set of parameters to 'smartly' update the parameter values and move quickly toward the best solution.

An example of an iterative algorithm may be the steepest descent algorithm. This algorithm computes the slope of the objective function at each iteration, and moves rapidly downhill to the nearest minimum solution. Another example algorithm which may be used is a Levenberg-Marquardt algorithm. In this algorithm, the curvature of the solution space is also taken into account in order to reach the nearest minimum in fewer steps.

With the linear and nonlinear components having been processed, method 100 may then output the fitted data at step 106. The data outputted at step 106 may be presented in any number of forms. In one embodiment, the step of outputting may comprise recovering the original model parameters utilizing the fitting dated derived in process 100. Such a recovery may be implemented as described above, or in any other manner suitable to provide output data in a form which is usable for a particular application.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for improving image processing for medical imaging systems that shows changes of at least one tracer as a function of time in a physiologic body, the method comprising:
    collecting image data measurements over a period of time, by the medical imaging system, at least by taking a series of measurements indicating a tracer concentration of the at least one tracer inputted into the physiologic body as the tracer distributes physiologically;
    receiving, at an image processing computer associated with the medical imaging systems, the image data measurements;
    preprocessing a plurality of tracer concentration curves that identify one or more underlying physiological processes of a living body that caused the tracer concentration to change over time by separating linear components of the tracer concentration curves from non-linear components of the tracer concentration curves;
    estimating which preprocessed tracer concentration curve of the preprocessed tracer concentration curves match the image data measurements at least by:
        fitting the linear components of the preprocessing tracer concentration curve to the image data measurements by reducing an amount of possible linear matches to a received region-of-interest, and then fitting the linear components to the received image data measurements, and
        fitting the non-linear components of the preprocessing tracer concentration curve to the image data measurements; and
    generating one or more image based at least on the matched preprocessed tracer concentration curve, wherein the one or more image identifies the one or more of the underlying physiological processes of the living body that caused the tracer concentration to change over time.

2. The method of claim 1 wherein the medical imaging systems include at least one of a dynamic SPECT, PET, CT, or MRI.

3. The method of claim 1 wherein the generated image digitally maps two or more tracers in the living body over the period time.

4. The method of claim 1 wherein the estimating which preprocessed tracer concentration curve of the preprocessed tracer concentration curves match the image data measurements comprises solving for the linear components in terms of the non-linear components and measured data in two steps using separate equations, in which case the linear components remain in a fitting equation but additional equations are presented that comprise constraints.

5. The method of claim 1 wherein fitting the-non-linear components of the matched preprocessed tracer concentration curve comprises utilizing an exhaustive search algorithm.

6. The method of claim 1 wherein the matched preprocessed tracer concentration curve for at least one of the tracers is a 5K model.

7. The method of claim 1 wherein fitting the non-linear components of the matched preprocessed tracer concentration curve comprises utilizing an iterative algorithm.

8. The method of claim 7 wherein the iterative algorithm is a fast gradient-decent algorithm.

9. The method of claim 7 wherein the iterative algorithm is at least one of a Levenberg-Marquardt, a Newton-Raphson, and a steepest-descent algorithm.

10. The method of claim 1 wherein the matched preprocessed tracer concentration curve for at least one of the tracers is one of a 2K, 3K, 4K and a 5K model.

11. The method of claim 1 wherein:
    the tracer is a drug;
    the series of measurements indicate a drug concentration; and
    the preprocessed tracer concentration curve is a pharmacokinetic model that describes changes in the drug concentration as the function of time.

12. A non-transitory computer-readable medium having program code recorded thereon, which causes a processor to improve image processing for medical imaging systems that show changes of at least one tracer as a function of time a physiologic body, the program code comprising:
    code for collecting image data measurements over a period of time, by medical imaging systems, at least by taking a series of measurements indicating a tracer concentration of the at least one tracer inputted into the physiologic body as the tracer distributes physiologically;
    code for receiving, at an image processing computer associated with the medical imaging systems, data measurements;
    code for preprocessing a plurality of tracer concentration curves that identify one or more of an underlying physiological processes of a living body that caused the tracer concentration to change over time by separating linear components of the tracer concentration curves from non-linear components of the tracer concentration curves;
    code for estimating which preprocessed tracer concentration curve of the preprocessed tracer concentration curves match the image data measurements at least by:

fitting the linear components of the preprocessing tracer concentration curve to the image data measurements by reducing an amount of possible linear matches to a received region-of-interest, and then fitting the linear components to the received image data measurements, and fitting the non-linear components of the preprocessing tracer concentration curve to the image data measurements; and code for generating one or more image based at least on the matched preprocessed tracer concentration curve, wherein the one or more image identifies the one or more of the underlying physiological processes of the living body that caused the tracer concentration to change over time.

13. The non-transitory computer-readable medium of claim 12 wherein the medical imaging systems include at least one of a dynamic SPECT, PET, CT, or MRI.

14. The non-transitory computer-readable medium of claim 12 wherein the generated image digitally maps two or more tracers in the living body over the period time.

15. The non-transitory computer-readable medium of claim 12 wherein the estimating which preprocessed tracer concentration curve of the preprocessed tracer concentration curves match the image data measurements comprises solving for the linear components in terms of the non-linear components and measured data in two steps using separate equations, in which case the linear components remain in a fitting equation but additional equations are presented that comprise constraints.

16. The non-transitory computer-readable medium of claim 12 wherein fitting the non-linear components of the matched preprocessed tracer concentration curve comprises utilizing an exhaustive search algorithm.

17. The non-transitory computer-readable medium of claim 12 wherein the matched preprocessed tracer concentration curve for at least one of the tracers is a 5K model.

18. The non-transitory computer-readable medium of claim 12 wherein fitting the non-linear components of the matched preprocessed tracer concentration curve comprises utilizing an iterative algorithm.

19. The non-transitory computer-readable medium of claim 18 wherein the iterative algorithm is a fast gradient-decent algorithm.

20. The non-transitory computer-readable medium of claim 18 wherein the iterative algorithm is at least one of a Levenberg-Marquardt, a Newton-Raphson, and a steepest-descent algorithm.

21. The non-transitory computer-readable medium of claim 12 wherein the matched preprocessed tracer concentration curve for at least one of the tracers is one of a 2K, 3K, 4K and a 5K model.

22. The non-transitory computer-readable medium of claim 12 wherein:
the tracer is a drug;
the series of measurements indicate a drug concentration; and
the preprocessed tracer concentration curve is a pharmacokinetic model that describes changes in the drug concentration as the function of time.

23. A system for improving image processing for medical imaging systems that shows changes of at least one tracer as a function of time in a physiologic body, the system comprising:
a memory; and
an image processing computer associated with the medical image systems that collects image data measurements over a period of time at least by taking a series of measurements indicating a tracer concentration of the at least one tracer inputted into the physiologic body as the tracer distributes physiologically, wherein the image processing computer further:
receives the image data measurements,
preprocesses a plurality of tracer concentration curves that identify one or more of an underlying physiological processes of a living body that caused the tracer concentration to change over time by separating linear components of the tracer concentration curves from non-linear components of the tracer concentration curves,
estimates which preprocessed tracer concentration curve of the preprocessed tracer concentration curves match the image data measurements at least by:
fitting the linear components of the preprocessing tracer concentration curve to the image data measurements by reducing an amount of possible linear matches to a received region-of-interest, and then fitting the linear components to the received image data measurements, and
fitting the non-linear components of the preprocessing tracer concentration curve to the image data measurements, and
generates one or more image based at least on the matched preprocessed tracer concentration curve, wherein the one or more image identifies the one or more of the underlying physiological processes of the living body that caused the tracer concentration to change over time.

24. The system of claim 23 wherein the medical imaging systems include at least one of a dynamic SPECT, PET, CT, or MRI.

25. The system of claim 23 wherein the generated image digitally maps two or more tracers in the living body over the period time.

26. The system of claim 23 wherein the estimating which preprocessed tracer concentration curve of the preprocessed tracer concentration curves match the image data measurements comprises solving for the linear components in terms of the non-linear components and measured data in two steps using separate equations, in which case the linear components remain in a fitting equation but additional equations are presented that comprise constraints.

27. The system of claim 23 wherein fitting the non-linear components of the matched preprocessed tracer concentration curve comprises utilizing an exhaustive search algorithm.

28. The system of claim 23 wherein the matched preprocessed tracer concentration curve for at least one of the tracers is a 5K model.

29. The system of claim 23 wherein fitting the non-linear components of the matched preprocessed tracer concentration curve comprises utilizing an iterative algorithm.

30. The system of claim 23 wherein the matched preprocessed tracer concentration curve for at least one of the tracers is one of a 2K, 3K, 4K and a 5K model.

31. The system of claim 23 wherein:
the tracer is a drug;
the series of measurements indicate a drug concentration; and
the preprocessed tracer concentration curve is a pharmacokinetic model that describes changes in the drug concentration as the function of time.

* * * * *